US012290812B2

United States Patent
Saadat et al.

(10) Patent No.: US 12,290,812 B2
(45) Date of Patent: May 6, 2025

(54) MICROFLUIDICS SYSTEM

(71) Applicant: MYMA MEDICAL LIMITED, Newcastle upon Tyne (GB)

(72) Inventors: Mozafar Saadat, Birmingham (GB); Arran James Richard Hughes, Birmingham (GB); Amir Mohammad Hajiyavand, Birmingham (GB)

(73) Assignee: MYMA MEDICAL LIMITED, Newcastle upon Tyne (GB)

( * ) Notice: Subject to any disclaimer, the term of this patent is extended or adjusted under 35 U.S.C. 154(b) by 1189 days.

(21) Appl. No.: 17/051,927

(22) PCT Filed: Apr. 30, 2019

(86) PCT No.: PCT/GB2019/051196
§ 371 (c)(1),
(2) Date: Oct. 30, 2020

(87) PCT Pub. No.: WO2019/211596
PCT Pub. Date: Nov. 7, 2019

(65) Prior Publication Data
US 2021/0121880 A1 Apr. 29, 2021

(30) Foreign Application Priority Data
Apr. 30, 2018 (GB) .................................... 1807001

(51) Int. Cl.
*B01L 3/00* (2006.01)
*C12N 5/076* (2010.01)
*G01N 33/68* (2006.01)

(52) U.S. Cl.
CPC ... *B01L 3/502738* (2013.01); *B01L 3/502715* (2013.01); *C12N 5/061* (2013.01);
(Continued)

(58) Field of Classification Search
CPC ....... B01L 3/502738; B01L 2300/0627; B01L 2300/163; B01L 2400/0478; B01L 2400/0487; B01L 2400/06; C12N 5/061
See application file for complete search history.

(56) References Cited

U.S. PATENT DOCUMENTS 3,069,654 A 12/1962 Hough
2005/0161112 A1* 7/2005 Ehwald ............. B01L 3/502738
141/130
(Continued)

FOREIGN PATENT DOCUMENTS

WO 2013040428 A1 3/2013

OTHER PUBLICATIONS

B. De Wagenaar et al: "Microfluidic single sperm entrapment and analysis", Lab on a Chip, vol. 15, No. 5, Jan. 1, 2015 (Jan. 1, 2015), pp. 1294-1301, XP55599796.
(Continued)

*Primary Examiner* — Matthew D Krcha
*Assistant Examiner* — Tingchen Shi
(74) *Attorney, Agent, or Firm* — David D. Brush; Westman, Champlin & Koehler, P.A.

(57) ABSTRACT

The disclosure relates to methods and systems for isolating individual sperm from a semen sample using microfluidics. Examples include a microfluidics system for isolating individual sperm from a semen sample, the system including: a first laminar flow channel extending between a first inlet and a first outlet; a second laminar flow channel extending between a second inlet and a second outlet; and a third laminar flow channel extending between the first and second laminar flow channels and having a restriction configured to prevent passage of a single sperm through the third laminar flow channel, wherein flow of a semen sample through the first laminar flow channel at a pressure higher than flow of
(Continued)

a liquid medium through the second laminar flow channel results in a single sperm being trapped by the restriction in the third laminar flow channel.

7 Claims, 12 Drawing Sheets

(52) U.S. Cl.
CPC .... *G01N 33/689* (2013.01); *B01L 2300/0627* (2013.01); *B01L 2300/163* (2013.01); *B01L 2400/0478* (2013.01); *B01L 2400/0487* (2013.01); *B01L 2400/06* (2013.01)

(56) References Cited

U.S. PATENT DOCUMENTS

| | | | |
|---|---|---|---|
| 2009/0068671 A1* | 3/2009 | Chakrabarty | G01N 33/56966 435/6.16 |
| 2014/0273179 A1 | 9/2014 | Sharpe et al. | |
| 2016/0016169 A1* | 1/2016 | Ben-Yakar | B01L 3/502738 506/40 |

OTHER PUBLICATIONS

Bjorn De Wagenaar et al: "Spermometer: electrical characterization of single boar sperm motility", Fertility and Sterility., vol. 106, No. 3, Sep. 1, 2016 (Sep. 1, 2016), pp. 773-780.e6, XP55599802.

Pankaj Talwar et al: "Microfluidics in andrology", Fertility Science and Research, vol. 4, No. 1, Jan. 1, 2017 (Jan. 1, 2017), pp. 8-14, XP55599875.

Hongyuan Huang: "Motile Human Sperm Sorting by an Integrated Microfluidic System", Journal of Nanomedicine & Nanotechnology, vol. 05, No. 03, Jan. 1, 2014 (Jan. 1, 2014), XP55599877.

W. Wang, X. Liu, D. Gelinas, B. Ciruna, and Y. Sun, 'A fully automated robotic system for microinjection of zebrafish embryos', PLoS One, vol. 2, No. 9, 2007.

A. Ghanbari, X. Chen, W. Wang, B. Horan, H. Abdi, and S. Nahavandi, 'Haptic microrobotic intracellular injection assistance using virtual fixtures', 11th Int. Conf. Control. Autom. Robot. Vision, ICARCV 2010, pp. 781-786, 2010.

A. Sieber et al., 'A novel haptic platform for real time bilateral biomanipulation with a MEMS sensor for triaxial force feedback', Sensors Actuators, A Phys., vol. 142, No. 1, pp. 19-27, 2008.

M. Ammi and A. Ferreira, 'Biological cell injection visual and haptic interface', Adv. Robot., vol. 20, No. Jan. 2015, pp. 283-304, 2006.

Y. Kimura and R. Yanagimachi, 'Intracytoplasmic sperm injection in the mouse', Biol Reprod, vol. 52, No. 4, pp. 709-720, 1995.

D. Kim, B. Kim, S. Yun, and S. Kwon, 'Cellular force measurement for force reflected biomanipulation', IEEE Int. Conf. Robot. Autom. 2004. Proceedings. ICRA '04. 2004, No. April, p. 2412-2417 vol. 3, 2004.

J. P. Desai, A. Pillarisetti, and A. D. Brooks, 'Engineering Approaches to Biomanipulation', Annu. Rev. Biomed. Eng., vol. 9, No. 1, pp. 35-53, 2007.

Z. Lu, P. C. Y. Chen, H. Luo, J. Nam, R. Ge, and W. Lin, 'Models of maximum stress and strain of zebrafish embryos under indentation', J. Biomech., vol. 42, No. 5, pp. 620-625, 2009.

M. Asgari, H. Abdi, C. P. Lim, and S. Nahavandi, 'Formulation and simulation of a 3D mechanical model of embryos for microinjection', Proc.—2013 IEEE Int. Conf. Syst. Man, Cybern. SMC 2013, pp. 2219-2224, 2013.

Z. Lu, P. C. Y. Chen, J. H. Nam, R. Ge, and W. Lin, 'A micromanipulation system for automatic batch microinjection', J. Micromechanics Microengineering, vol. 17, pp. 314-321, 2007.

A. Pillarisetti, S. Member, M. Pekarev, A. D. Brooks, J. P. Desai, and A. Member, 'Evaluating the Effect of Force Feedback in Cell Injection', vol. 4, No. 3, pp. 322-331, 2007.

Y. Xie, D. Sun, C. Liu, H. Y. Tse, and S. H. Cheng, 'A Force Control Approach to a Robotassisted Cell Microinjection System', Int. J. Rob. Res., vol. 29, No. 9, pp. 1222-1232, 2010.

Deok-Ho Kim, Seok Yun, and Byungkyu Kim, 'Mechanical force response of single living cells using a microrobotic system', IEEE Int. Conf. Robot. Autom., pp. 5013-5018, 2004.

Xinyu Liu, K. Kim, Yong Zhang, and Yu Sun, 'Nanonewton Force Sensing and Control in Microrobotic Cell Manipulation', Int. J. Rob. Res., vol. 28, No. 8, pp. 1065-1076, 2009.

P. C. Y. Chen et al., 'Speed optimization in automated microinjection of zebrafish embryos', Int. J. Control. Autom. Syst., vol. 13, No. 5, pp. 1233-1241, 2015.

Kim, D.H., Sun, Y., Yun, S., Kim, B., Hwang, C.N., Lee, S.H. and Nelson, B.J., Sep. 2004. Mechanical property characterization of the zebrafish embryo chorion. In Engineering in Medicine and Biology Society, 2004. IEMBS'04. 26th Annual International Conference of the IEEE (vol. 2, pp. 5061-5064). IEEE.

Hajiyavand, A.M., Saadat, M. and Bedi, A.P.S., Jul. 2016. Polar body detection for ICSI cell manipulation. In Manipulation, Automation and Robotics at Small Scales (MARSS), International Conference on (pp. 1-6). IEEE.

Hogan, Brigid, Frank Costantini, and Elizabeth Lacy. Manipulating the mouse embryo: a laboratory manual. vol. 34. Cold Spring Harbor, NY: Cold spring harbor laboratory, 1986.

Hogg, R.C.; Bandelier, F.; Benoit, A.; Dosch, R.; Bertrand, D. An automated system for intracellular and intranuclear Injection. Journal of neuroscience methods 2008, 169, 65-75.

Wang, Z.; Latt, W.T.; Tan, S.Y.M.; Ang, W.T. Visual servoed three-dimensional cell rotation system. IEEE Transactions on Biomedical Engineering 2015, 62, 2498-2507.

Lu, Z.; Zhang, X.; Leung, C.; Esfandiari, N.; Casper, R.F.; Sun, Y. Robotic icsi (intracytoplasmic sperm injection). IEEE Transactions on Biomedical Engineering 2011, 58, 2102-2108.

Feng, L.; Turan, B.; Ningga, U.; Arai, F. Three dimensional rotation of bovine oocyte by using magnetically driven on-chip robot, Intelligent Robots and Systems (IROS 2014), 2014 IEEE/RSJ International Conference on, 2014; IEEE: pp. 4668-4673.

Zhao, Q.; Sun, M.; Cui, M.; Yu, J.; Qin, Y.; Zhao, X. Robotic cell rotation based on the minimum rotation force. IEEE Transactions on Automation Science and Engineering 2015, 12, 1504-1515.

Nan, Z. and Xu, Q., 2017, July. Multiple-cell recognition and path planning for robotic microinjection system. In Control Conference (CCC), 2017 36th Chinese (pp. 6691-6696). IEEE.

Wang, Z., Feng, C., Ang, W.T., Tan, S.Y.M. and Latt, W.T. Autofocusing and polar body detection in automated cell manipulation. IEEE Transactions on Biomedical Engineering, 2017, 64(5), pp. 1099-1105.

Boukallel, M.; Gauthier, M.; Dauge, M.; Piat, E.; Abadie, J. Smart microrobots for mechanical cell characterization and cell convoying. IEEE transactions on biomedical engineering 2007, 54, 1536-1540.

Janocha, H. In Microactuators-principles, applications, trends, Proc. Micro. tec 2000, VDE World Microtechnology Congress, 2000; pp. 25-27.

Leung, C.; Lu, Z.; Zhang, X.P.; Sun, Y. Three-dimensional rotation of mouse embryos. IEEE Transactions on Biomedical Engineering 2012, 59, 1049-1056.

Nguyen, B.V.; Wang, Q.G.; Kuiper, N.J.; El Haj, A.J.; Thomas, C.R.; Zhang, Z. Biomechanical properties of single chondrocytes and chondrons determined by micromanipulation and finiteelement modelling. Journal of the Royal Society Interface 2010, 7, 1723-1733.

Mohanty, S.K.; Gupta, P.K. Laser-assisted three-dimensional rotation of microscopic objects. Review of scientific Instruments 2004, 75, 2320-2322.

Shen, Y.; Fukuda, T. State of the art: Micro-nanorobotic manipulation in single cell analysis. Robotics and Biomimetics Jan. 21, 2014.

Chronis, N.; Lee, L.P. Polymer mems-based microgripper for single cell manipulation, Micro Electro Mechanical Systems, 2004. 17th IEEE International Conference on (MEMS), 2004; IEEE: pp. 17-20.

Jager, E.W.; Inganas, O.; Lundstrom, I. Microrobots for micrometer-size objects in aqueous media: Potential tools for single-cell manipulation. Science 2000, 288, 2335-2338.

(56) References Cited

OTHER PUBLICATIONS

Ichikawa, A.; Sakuma, S.; Shoda, T.; Arai, F.; Akagi, S. On-chip enucleation of oocyte using untetherd micro-robot with gripping mechanism, Micro-NanoMechatronics and Human Science (MHS), 2013 International Symposium on, 2013; IEEE: pp. 1-3.
Zhang, Y.; Tan, K.K.; Huang, S. Vision-servo system for automated cell injection. IEEE Transactions on Industrial Electronics 2009, 56, 231-238.
Shin, Y.K.; Kim, Y.; Kim, J. Automated microfluidic system for orientation control of mouse embryos, Intelligent Robots and Systems (IROS), 2013 IEEE/RSJ International Conference on, 2013; IEEE: pp. 496-501.
Otsu, N. A threshold selection method from gray-level histograms. IEEE transactions on systems, man, and cybernetics 1979, 9, 62-66.
Chen, D., Sun, M. and Zhao, X. Oocytes polar body detection for automatic enucleation. Micromachines, 2016, 7(2), p. 27.
Zhao, Q., Cui, M., Zhang, C., Yu, J., Sun, M. and Zhao, X., Apr. 2014. Robotic enuleation for oocytes. In Nano/Micro Engineered and Molecular Systems (NEMS), 2014, 9th IEEE International Conference on (pp. 23-27). IEEE.
Sun, Y.; Nelson, B.J. Biological cell injection using an autonomous microrobotic system. The International Journal of Robotics Research 2002, 21, 861-868.
Du, Q.; Zhang, Q.; Tian, L.; Wu, Z. Object detection and tracking for a vision guided automated suspended cell Injection process, Mechatronics and Automation (ICMA), 2010 International Conference on, 2010; IEEE: pp. 1760-1764.
Rienzi, L.; Balaban, B.; Ebner, T.; Mandelbaum, J. The oocyte. Human Reproduction 2012, 27, i2-i21.
Al-Amri, S.S.; Kalyankar, N.; Khamitkar, S. Linear and non-linear contrast enhancement image. International Journal of Computer Science and Network Security 2010, 10, 139-143.
Priya, S.; Kumar, T.A.; Paul, V. A novel approach to fabric defect detection using digital image processing, Signal Processing, Communication, Computing and Networking Technologies (ICSCCN), 2011 International Conference on, 2011; IEEE: pp. 228-232.
Caponetti, L.; Castellano, G.; Basile, M.T.; Corsini, V. Fuzzy mathematical morphology for biological image segmentation. Applied intelligence 2014, 41, 117-127.
Malter, Henry E. "Micromanipulation in assisted reproductive technology." Reproductive biomedicine online 32, No. 4 (2016): 339-347.
D. Beebe, M. Wheeler, H. Zeringue, E. Walters, and S. Raty, "Microfluidic technology for assisted reproduction," Theriogenology, vol. 57, No. 1, pp. 125-135, 2002.
Hogg, Ron C., Florence Bandelier, Audrey Benoit, Roland Dosch, and Daniel Bertrand. "An automated system for Intracellular and intranuclear injection." Journal of neuroscience methods 169, No. 1 (2008): 65-75.
Wang, Zenan, Win Tun Latt, Steven Yih Min Tan, and Wei Tech Ang. "Visual Servoed Three-Dimensional Cell Rotation System." IEEE Transactions on Biomedical Engineering 62, No. 10 (2015): 2498-2507.
Lu, Zhe, Xuping Zhang, Clement Leung, Navid Esfandiari, Robert F. Casper, and Yu Sun. "Robotic ICSI (intracytoplasmic sperm injection)." IEEE Transactions on Biomedical Engineering 58, No. 7 (2011): 2102-2108.
S. Muntwyler, F. Beyeler, and B. J. Nelson, "Three-axis micro-force sensor with sub-micronewton measurement uncertainty and tunable force range," J. Micromech. Microeng., vol. 20, No. 2, 2010.
F. Beyeler et al., "Monolithically fabricated microgripper with integrated force sensor for manipulating microobjects and biological cells aligned in an ultrasonic field," J. Microelectromech. Syst., vol. 16, pp. 7-15, Feb. 2007.
K. Kim, X. Liu, Y. Zhang, and Y. Sun, "Nanonewton force-controlled manipulation of biological cells using a monolithic MEMS microgripper with two-axis force feedback," J. Micromech. Microeng., vol. 18, No. 5, 2008.
B. Solano and D. Wood, "Design and testing of a polymeric microgripper for cell manipulation," Microelectron. Eng., vol. 84, Nos. 5-8, pp. 1219-1222, 2007.
B. Solano, A. Gallant, and D. Wood, "Design and optimisation of a microgripper: Demonstration of biomedical applications using the manipulation of oocytes," in Proc. Symp. Design, Test, Integr. Packag., Apr. 2009, pp. 61-65.
S. Raty et al. "Embryonic development in the mouse is enhanced via microchannel culture," Lab Chip, vol. 4, pp. 186-190, 2004.
Leung, Clement, Zhe Lu, Xuping P. Zhang, and Yu Sun. "Three-dimensional rotation of mouse embryos." IEEE Transactions on Biomedical Engineering59, No. 4 (2012): 1049-1056.
R. Ma et al., "In vitro fertilization on a single-oocyte positioning system integrated with motile sperm selection and early embryo development," Anal. Chem., vol. 83, No. 8, pp. 2964-2970, 2011.
C. Han et al., "Integration of single oocyte trapping, in vitro fertilization and embryo culture in a microwell-structured microfluidic device," Lab Chip, vol. 10, pp. 2848-2854, 2010.
Benhal, Prateek, J. Geoffrey Chase, Paul Gaynor, Bjorn Oback, and Wenhui Wang. "AC electric field induced dipole-based on-chip 3D cell rotation." Lab on a Chip 14, No. 15 (2014): 2717-2727.
Arnold, W. Michael, Rita K. Schmutzler, Andreas G. Schmutzler, Hans van der Ven, Safaa Al-Hasani, Dieter Krebs, and Ulrich Zimmermann. "Electro-rotation of mouse oocytes: single-cell measurements of zona-intact and zona-free cells and of the isolated zona pellucida." Biochimica et Biophysica Acta (BBA)—Biomembranes 905, No. 2 (1987): 454-464.
Liang, Yuan-Li, Yuan-Peng Huang, Yen-Sheng Lu, Max T. Hou, and J. Andrew Yeh. "Cell rotation using optoelectronic tweezers." Biomicrofluidics4, No. 4 (2010): 043003.
Jager, Edwin WH, Olle Inganas, and Ingemar Lundstrom. "Microrobots for micrometer-size objects in aqueous media: potential tools for single-cell manipulation." Science 288, No. 5475 (2000): 2335-2338.
Thakur, Atul, Sagar Chowdhury, Petr Svec, Chenlu Wang, Wolfgang Losert, and Satyandra K. Gupta. "Indirect pushing based automated micromanipulation of biological cells using optical tweezers." The International Journal of Robotics Research (2014): 0278364914523690.
W. T. Coakley, D. W. Bardsley, M. A. Grundy, F. Zamani, and D. J. Clarke, "Cell manipulation in ultrasonic standing wave fields," J. Chem. Technol. Biotechnol., vol. 44, No. 1, pp. 43-62, 1989.
Sun, Yu, and Bradley J. Nelson. "Biological cell injection using an autonomous microrobotic system." The International Journal of Robotics Research 21, No. 10-11 (2002): 861-868.
Huang, Haibo B., Dong Sun, James K. Mills, and Shuk Han Cheng. "Robotic cell injection system with position and force control: toward automatic batch biomanipulation." IEEE transactions on robotics 25, No. 3 (2009): 727-737.
Lu, Zhe, Peter CY Chen, Joohoo Nam, Ruowen Ge, and Wei Lin. "A micromanipulation system with dynamic force-feedback for automatic batch microinjection." Journal of micromechanics and microengineering 17, No. 2 (2007): 314.
Lu, Zhe, Xuping Zhang, Clement Leung, Navid Esfandiari, Robert F. Casper, and Yu Sun. "Automated cell manipulation: Robotic ICSI." In Robotics and Automation (ICRA), 2011 IEEE International Conference on, pp. 2540-2545. IEEE, 2011.
Yanaihara, A., Iwasaki, S., Negishi, M. and Okai, T., 2005. Intracytoplasmic Sperm Injection: Technical Improvement. Taiwanese Journal of Obstetrics and Gynecology, 44(4), pp. 314-317.
Bahadur, I.M. and Mills, J.K., Jul. 2012. Dynamic model of micropipettes in piezo-assisted icsi. In Complex Medical Engineering (CME), 2012 ICME International Conference on (pp. 191-196). IEEE.
Bahadur, I.M. and Mills, J.K., May 2013. A mechanical perforation procedure for embryo biopsy. In Complex Medical Engineering (CME), 2013 ICME International Conference on (pp. 313-318). IEEE.
International Search Report dated Jun. 27, 2019 for corresponding International Application No. PCT/GB2019/051196, filed Apr. 30, 2019.
Written Opinion of the International Searching Authority dated Jun. 27, 2019 for corresponding International Application No. PCT/GB2019/051196, filed Apr. 30, 2019.

(56) References Cited

OTHER PUBLICATIONS

International Preliminary Report on Patentability and English translation of the Written Opinion of the International Searching Authority dated Nov. 3, 2020 for corresponding International Application No. PCT/GB2019/051196, iled Apr. 30, 2019.
Search Report dated Nov. 7, 2018, for corresponding GB1807001.1 filed Apr. 30, 2018.
J. Datta, M.J. Palmer, C. Tanton, L.J. Gibson, K.G. Jones, W. Macdowall, A. Glasier, p. Sonnenberg, N. Field, C.H. Mercer, A.M. Johnson, K. Wellings; Prevalence of infertility and help seeking among 15 000 women and men, Human Reproduction, vol. 31, Issue 9, Sep. 1, 2016, pp. 2108-2118.
Marcia C. Inhorn, Pasquale Patrizio; Infertility around the globe: new thinking on gender, reproductive technologies and global movements in the 21st century, Human Reproduction Update, vol. 21, Issue 4, Jul. 1, 2015, pp. 411-426.
Bungum, M., P. Humaidan, M. Spano, K. Jepson, L. Bungum, and Aleksander Giwercman. "The predictive value of sperm chromatin structure assay (SCSA) parameters for the outcome of intrauterine insemination, IVF and ICSI." Human Reproduction 19, No. 6 (2004): 1401-1408.
Andersen, A. Nyboe, V. Goossens, L. Gianaroli, R. Felberbaum, J. De Mouzon, and K. G. Nygren. "Assisted reproductive technology in Europe, 2003. Results generated from European registers by ESHRE." Human Reproduction (2007).
Fertility Treatments. (n.d.). Retrieved Nov. 6, 2016, from Newlife IVF: https://www.newlifeivf.co.uk/fertility-treatments.php.
Hill, M.A. (2016) Embryology Oocyte Development. Retrieved Nov. 5, 2016, From https://embryology.med.unsw.edu.au/embryology/index.php/Oocyte_Development.
Gerris, Jan MR. "Single embryo transfer and IVF/ICSI outcome: a balanced appraisal." Human Reproduction Update 11, No. 2 (2005): 105-121.
Ladjal, Hamid, Jean-Luc Hanus, and Antoine Ferreira. "Microrobotic simulator for assisted biological cell injection." In 2011 IEEE/RSJ International Conference on Intelligent Robots and Systems, pp. 1315-1320. IEEE, 2011.
Ladjal, Hamid, Jean-Luc Hanus, and Antoine Ferreira. "Micro-to-nano biomechanical modeling for assisted biological cell injection." IEEE Transactions on Biomedical Engineering 60, No. 9 (2013): 2461-2471.
Kastrop, P. M. M., S. M. Weima, R. J. Van Kooij, and E. R. Te Velde. "Comparison between intracytoplasmic sperm injection and in-vitro fertilization (IVF) with high insemination concentration after total fertilization failure in a previous IVF attempt." Human Reproduction 14, No. 1 (1999): 65-69.
Ebner, Thomas, Cemil Yaman, Marianne Moser, Michael Sommergruber, Klaus Jesacher, and Gernot Tews. "A prospective study on oocyte survival rate after ICSI: influence of injection technique and morphological features." Journal of assisted reproduction and genetics 18, No. 12 (2001): 623-628.
Dumoulin, John CM, Edith Coonen, Marijke Bras, J. Marij Bergers-Janssen, Rosie CM Ignoul-Vanvuchelen, Lucie CP van Wissen, Joep PM Geraedts, and Johannes LH Evers. "Embryo development and chromosomal anomalies after ICSI: effect of the injection procedure." Human Reproduction 16, No. 2 (2001): 306-312.
Agarwal, Ashok, Kartikeya Makker, and Rakesh Sharma. "Review article: clinical relevance of oxidative stress in male factor infertility: an update." American Journal of Reproductive Immunology 59, No. 1 (2008): 2-11.
Gabrielsen, A., S. Lindenberg, and K. Petersen. "The impact of the zona pellucida thickness variation of human embryos on pregnancy outcome in relation to suboptimal embryo development. A prospective randomized controlled study." Human Reproduction 16, No. 10 (2001): 2166-2170.
G. D. Palermo et al., 'Oolemma characteristics in relation to survival and fertilization patterns of oocytes treated by Intracytoplasmic sperm injection.', Hum. Reprod., vol. 11, No. I, pp. 172-176, 1996.
M. A. Danfour and M. S. Elmahaishi, 'Human oocyte oolemma characteristic is positively related to embryo developmental competence after ICSI procedure', Middle East Fertil. Soc. J., vol. 15, No. 4, pp. 269-273, 2010.
M. Khalilian, M. R. Valojerdi, M. Navidbakhsh, M. Chizari, and P. Eftekhari-Yazdi, 'Estimating zona pellucida hardness under microinjection to assess oocyte/embryo quality: Analytical and experimental studies', Adv. Biosci. Biotechnol., vol. 4, pp. 679-688, 2013.
K. Yanagida, H. Katayose, H. Yazawa, Y. Kimura, K. Konnai, and A. Sato, 'The usefulness of a piezo-micromanipulator in intracytoplasmic sperm injection in humans.', Hum. Reprod., vol. 14, No. 2, pp. 448-453, 1998.
J. M. R. Gerris, 'Single embryo transfer and IVF/ICSI outcome: A balanced appraisal', Hum. Reprod. Update, vol. 11, No. 2, pp. 105-121, 2005.
Y. Kawase, T. Iwata, Y. Toyoda, T. Wakayama, R. Yanagimachi, and H. Suzuki, 'Comparison of intracytoplasmic sperm injection for inbred and hybrid mice', Mol. Reprod. Dev., vol. 60, No. 1, pp. 74-78, 2001.
Y. Kawase et al., 'Effect of partial incision of the zona pellucida by piezo-micromanipulator for in vitro fertilization using frozen-thawed mouse spermatozoa on the developmental rate of embryos transferred at the 2-cell stage.', Biol. Reprod., vol. 66, No. 2, pp. 381-385, 2002.
A. F. Ergenc, M. W. Li, M. Toner, J. D. Biggers, K. C. K. Lloyd, and N. Olgac, 'Rotationally oscillating drill (Ros-Drill ©) for mouse ICSI without using mercury', Mol. Reprod. Dev., vol. 75, No. 12, pp. 1744-1751, 2008.
A. F. Ergenc and N. Olgac, 'New technology for cellular piercing: Rotationally oscillating u-injector, description and validation tests', Biomed. Microdevices, vol. 9, No. 6, pp. 885-891, 2007.
L. Rienzi, E. Greco, F. Ubaldi, M. Iacobelli, F. Martinez, and J. Tesarik, 'Laser-assisted intracytoplasmic sperm Injection', Fertil. Steril., vol. 76, No. 5, pp. 1045-1047, 2001.
S. Abdelmassih, J. Cardoso, V. Abdelmassih, J. a Dias, R. Abdelmassih, and Z. P. Nagy, 'Laserassisted ICSI: a novel approach to obtain higher oocyte survival and embryo quality rates.', Hum. Reprod., vol. 17, No. 10, pp. 2694-2699, 2002.
Y. Murayama et al., 'Elasticity Measurement of Zona Pellucida Using a Micro Tactile Sensor to Evaluate Embryo Quality', J. Mamm. Ova Res., vol. 25, No. 1, pp. 8-16, 2008.
Y. Murayama, C. E. Constantinou, and S. Omata, 'Micromechanical sensing platform for the characterization of the elastic properties of the ovum via uniaxial measurement', J. Biomech., vol. 37, No. 1, pp. 67-72, 2004.
Y. Murayama et al., 'Mouse zona pellucida dynamically changes its elasticity during oocyte maturation, fertilization and early embryo development.', Hum. cell Off. J. Hum. Cell Res. Soc., vol. 19, No. 4, pp. 119-125, 2006.
M. Khalilian, M. Navidbakhsh, M. R. Valojerdi, M. Chizari, and P. E. Yazdi, 'Estimating Young's modulus of zona pellucida by micropipette aspiration in combination with theoretical models of ovum', J. R. Soc. Interface, vol. 7, No. 45, pp. 687-694, 2010.
Yu Sun, Kai-Tak Wan, K. P. Roberts, J. C. Bischof, and B. J. Nelson, 'Mechanical property characterization of mouse zona pellucida', IEEE Trans. Nanobioscience, vol. 2, No. 4, pp. 279-286, 2003.
Y. Hiramoto and S. Nakamura, 'Mechanical properties of the cell surface in starfish eggs', vol. 20, No. 4, pp. 317-327, 1978.
A. Pillarisetti, J. P. Desai, H. Ladjal, A. Schiffmacher, A. Ferreira, and C. L. Keefer, 'Mechanical Phenotyping of Mouse Embryonic Stem Cells: Increase in Stiffness with Differentiation', Cell. Reprogramming (Formerly 'Cloning Stem Cells'), vol. 13, No. 4, pp. 371-380, 2011.
B. V. Derjaguin, V. M. Muller, and Y. U. P. Toporov, 'Effect of contact deformation on the adhesion of particles.', J. Colloid Interface Sci., vol. 53, No. 2, pp. 314-326, 1975.
Z. Zhang, M. A. Ferenczi, and C. R. Thomas, 'A micromanipulation technique with a theoretical cell model for determining mechanical properties of single mammalian cells', Chem. Eng. Sci., vol. 47, No. 6, pp. 1347-1354, 1992.
H. Huang, J. K. Mills, C. Lu, and D. Sun, 'A universal piezo-driven ultrasonic cell microinjection system', Biomed. Microdevices, vol. 13, No. 4, pp. 743-752, 2011.

(56) References Cited

OTHER PUBLICATIONS

Y. Xie, D. Sun, C. Liu, and S. H. Cheng, 'An adaptive impedance force control approach for robotic cell microinjection', 2008 IEEE/RSJ Int. Conf. Intell. Robot. Syst. IROS, pp. 907-912, 2008.

Y. Xie, D. Sun, C. Liu, S. H. Cheng, and Y. H. Liu, 'A force control based cell injection approach in a bio-robotics system', Proc.—IEEE Int. Conf. Robot. Autom., pp. 3443-3448, 2009.

S. D. Tan Y Huang W, Cheng SH., 'Mechanical modeling of biological cells in microinjection.', IEEE Trans Nanobioscience, vol. 7, No. 4, pp. 257-266, 2008.

G. Gilardi and I. Sharf, 'Literature survey of contact dynamics modelling', Mech. Mach. Theory, vol. 37, No. 10, pp. 1213-1239, 2002.

Lu, Zhe, Peter CY Chen, Hong Luo, Joohoo Nam, Ruowen Ge, and Wei Lin. "Models of maximum stress and strain of zebrafish embryos under indentation." Journal of biomechanics 42, No. 5 (2009): 620-625.

Vassilev, V.M., Kostadinov, K.G., Mladenov, I.M., Shulev, A.A., Stoilov, G.I. and Djondjorov, P.A., Apr. 2011. Cell Membranes Under Hydrostatic Pressure Subjected to Micro-Injection. In AIP Conference Proceedings (vol. 1340, No. 1, pp. 234-240). AIP.

Lin, Y.L., Wang, D.M., Lu, W.M., Lin, Y.S. and Tung, K.L., 2008. Compression and deformation of soft spherical particles. Chemical Engineering Science, 63(1), pp. 195-203.

S. Takeuchi, H. Minoura, T. Shibahara, X. Shen, N. Futamura, and N. Toyoda, 'Comparison of piezo-assisted micromanipulation with conventional micromanipulation for intracytoplasmic sperm injection into human oocytes', Gynecol. Obstet. Invest., vol. 52, No. 3, pp. 158-162, 2001.

K. Yanagida, H. Katayose, H. Yazawa, Y. Kimura, K. Konnai, and a Sato, 'The usefulness of a piezo-micromanipulator in intracytoplasmic sperm injection in humans.', Hum. Reprod., vol. 14, No. 2, pp. 448-453, 1999.

Z. Lu, X. Zhang, C. Leung, N. Esfandiari, R. F. Casper, and Y. Sun, 'Robotic ICSI (Intracytoplasmic Sperm Injection)', IEEE Trans. Biomed. Eng., vol. 58, No. 7, pp. 2102-2108, 2011.

\* cited by examiner

MICROFLUIDICS SYSTEM

CROSS-REFERENCE TO RELATED APPLICATIONS

This Application is a Section 371 National Stage Application of International Application No. PCT/GB2019/051196, filed Apr. 30, 2019, which is incorporated by reference in its entirety and published as WO 2019/211596 A1 on Nov. 7, 2019, not in English.

FIELD OF THE INVENTION

The invention relates to components, methods and a system for intracytoplasmic sperm injection, including methods and systems for detecting the orientation of an oocyte and its polar body, methods and systems for intracytoplasmic sperm injection and methods and systems for isolating individual sperm from a semen sample using microfluidics.

BACKGROUND

Intracytoplasmic sperm injection (ICSI) is a clinical method for infertility treatment, in which a single sperm is selected, immobilised and deposited within an oocyte. Current technologies for performing ICSI typically rely on manual control, which can lead to human error resulting in damage to the oocyte due to lack of control of the procedure and deformation of the oocyte during the injection procedure.

Currently, during an ICSI operation approximately 10% of injected oocytes are destroyed. The reasons for this are unclear but one major cause may relate to mechanical deformation during the injection procedure. During injection, the introduction of a microneedle results in damage to the oocyte due to introducing the deformation on the zona pellucida and oolemma (external membranes), which may produce deformities within the structure of the oocyte.

Current microinjection procedures are largely manual (although using a mechanised system), and tracking is purely through visual observation using images from a microscope. The embryologist (operator) determines whether or not injection has taken place by observing the presence (or absence) of deformation from 2D images of the oocyte. This means that the embryologist must observe deformation taking place in order to ascertain that injection has indeed taken place. This means that occurrence of oocyte deformation is (undesirably) a pre-requisite for every injection in the current practice.

Current practice offers no injection force-feedback to allow the embryologist sufficient control over the process. This effectively means that the operator has no information while performing the injection other than visual feedback, which can lead to human error during the injection process.

As an alternative to needle injection, there has been recent research into robotic micro manipulation systems and control including piezoelectric-actuated microgrippers and micro tele-manipulation control. Problems with these current methods such as the piezoelectric microgripper include an introduction of a mercury column to minimise vibration, but this material is toxic and can lead to cell degeneration. Tele-manipulation control systems create a wound on the cell membrane, which also damages the cell.

SUMMARY OF THE INVENTION

In accordance with a first aspect there is provided a microfluidics system for isolating individual sperm from a semen sample, the system comprising:
  a first laminar flow channel extending between a first inlet and a first outlet;
  a second laminar flow channel extending between a second inlet and a second outlet; and
  a third laminar flow channel extending between the first and second laminar flow channels and having a restriction configured to prevent passage of a single sperm through the third laminar flow channel,
  wherein flow of a semen sample through the first laminar flow channel at a pressure higher than flow of a liquid medium through the second laminar flow channel results in a single sperm being trapped by the restriction in the third laminar flow channel.

The system may comprise:
  a fourth laminar flow channel connected between the first laminar flow channel and a third outlet;
  a first valve in the first laminar flow channel between the first inlet and the third laminar flow channel;
  a second valve in the first laminar flow channel between the fourth laminar flow channel and the first outlet; and
  a third valve in the fourth laminar flow channel between the first laminar flow channel and the third outlet,
  wherein, upon closing the first and second valves and opening the third valve, a sperm trapped by the restriction in the third laminar flow channel travels to the third outlet for collection.

The third outlet may comprise a chamber with an internal surface coated with an antisperm antibody. The antisperm antibody may for example be an Immunoglobulin G isotype. The use of such an antibody may result in the single sperm being immobilised in the chamber, or at least result in a reduced motility, so that the sperm can be more readily transferred to a microneedle for injection.

The system may comprise a flow sensor configured to sense fluid flow in the third laminar flow channel.

The system may comprise:
  a first pump arranged to pump fluid into the first inlet at a first pressure;
  a second pump arranged to pump fluid into the second inlet at a second pressure lower than the first pressure; and
  a controller configured to control the first and second pumps, operate the first, second and third valves and receive a flow signal from the flow sensor,
  wherein the controller is configured to close the first and second valves upon detecting a reduction in flow through the third laminar flow channel from the flow sensor and to open the fourth valve to cause fluid from the second laminar flow channel to flow through the third laminar flow channel, the first laminar flow channel and towards the third outlet.

The pumps, and optionally also the controller, may be integrated with the microfluidics system on a single 'lab on a chip' device.

In accordance with a second aspect, there is provided a method of operating a microfluidics system, the system comprising:
  a first laminar flow channel extending between a first inlet and a first outlet;
  a second laminar flow channel extending between a second inlet and a second outlet; and
  a third laminar flow channel extending between the first and second laminar flow channels and having a restriction configured to prevent passage of a single sperm through the third laminar flow channel, wherein the method comprises:
introducing a semen sample into the first laminar flow channel at a first pressure;
introducing a fluid transport medium into the second laminar flow channel at a second pressure lower than the first pressure; and
trapping a single sperm in the restriction in the third laminar flow channel.

The system may further comprise:
a fourth laminar flow channel connected between the first laminar flow channel and a third outlet;
a first valve in the first laminar flow channel between the first inlet and the third laminar flow channel;
a second valve in the first laminar flow channel between the fourth laminar flow channel and the first outlet; and
a third valve in the fourth laminar flow channel between the first laminar flow channel and the third outlet,
and the method may further comprise:
detecting a reduction in flow through the third laminar flow channel;
closing the first and second valves; and
opening the third valve to cause a sperm trapped by the restriction in the third laminar flow channel to travel to the third outlet for collection.

The system may comprise a flow sensor configured to sense fluid flow in the third laminar flow channel, wherein detecting a reduction in flow through the third laminar flow channel comprises receiving a signal from the flow sensor.

The system may further comprise:
a first pump arranged to pump fluid into the first inlet at a first pressure;
a second pump arranged to pump fluid into the second inlet at a second pressure lower than the first pressure; and
a controller configured to control the first and second pumps, operate the first, second and third valves and receive a flow signal from the flow sensor,
wherein the method comprises:
the controller closing the first and second valves upon detecting a reduction in reduction in flow through the third laminar flow channel from the flow sensor; and
the controller opening the fourth valve to cause fluid from the second laminar flow channel to flow through the third laminar flow channel, the first laminar flow channel and towards the third outlet.

The system may comprise a fifth valve over the restriction, and the method may comprise closing the fifth valve following the step of trapping a single sperm in the restriction. The fifth valve may then be opened prior to opening the third valve to cause the sperm trapped by the restriction in the third laminar flow channel to travel to the third outlet for collection.

In accordance with a third aspect there is provided a microfluidics system for containing and immobilising an individual sperm, the system comprising a chamber connected to a laminar flow channel for introduction of the individual sperm in a carrier fluid, wherein an internal surface of the chamber is coated with an antisperm antibody. The antisperm antibody may be an Immunoglobulin G isotype.

In accordance with a fourth aspect of the invention there is provided an automated method for detection of an orientation of an oocyte, the method comprising the steps of:
i) acquiring an image of the oocyte;
ii) defining first and second elliptical features in the image based on edges detected in the image;
iii) calculating an orientation of the second elliptical feature relative to the first elliptical feature; and
iv) outputting a relative orientation of a polar body of the oocyte based on the orientation of the second elliptical feature relative to the first elliptical feature.

An advantage of the invention is that an orientation of the polar body can be automatically determined from a single image, which allows the oocyte to be reoriented automatically to place the polar body in a preferred position for injection to take place, thereby reducing the potential for human error.

Step iii) of the method may comprise:
calculating a first angular component in a focal plane of the image between a base line and a line connecting centre points of the first and second elliptical features; and
calculating a second angular component relative to the focal plane from a calculated distance in the focal plane between the centre points of the first and second elliptical features and calculated radii of the first and second elliptical features.

Step ii) may comprise applying a weighted filter to the acquired image to reduce noise in the image.

Step ii) may comprise employing a circular or elliptical Hough transform to the acquired image to define the first and second elliptical features.

Step ii) may further comprise:
computing image gradients across the image;
calculating a gradient magnitude across the image; and
applying the circular or elliptical Hough transform to pixels in the image having a gradient magnitude above a threshold value.

A position of the polar body above or below a focal plane of the image may be determined according to an intensity of the second elliptical feature relative to a threshold intensity. The polar body may for example be determined to be above the focal plane if the intensity of the second elliptical feature is below the threshold intensity and below the focal plane if the intensity of the second elliptical feature is above the threshold intensity.

In accordance with a fifth aspect, there is provided a system for detecting and orienting an oocyte, the system configured to:
acquire an image of the oocyte;
define first and second elliptical features in the image based on edges detected in the image;
calculate an orientation of the second elliptical feature relative to the first elliptical feature; and
output a relative orientation of a polar body of the oocyte based on the orientation of the second elliptical feature relative to the first elliptical feature.

The system may be further configured to:
calculate a first angular component in a focal plane of the image between a base line and a line connecting centre points of the first and second elliptical features; and
calculate a second angular component relative to the focal plane from a calculated distance in the focal plane between the centre points of the first and second elliptical features and calculated radii of the first and second elliptical features.

The system may be further configured to apply a weighted filter to the acquired image to reduce noise in the image.

The system may be further configured to employ a circular of elliptical Hough transform to the acquired image to define the first and second elliptical features.

The system may be configured to determine a position of the polar body to be above or below a focal plane of the image is according to an intensity of the second elliptical feature relative to a threshold intensity. The polar body may for example be determined to be above the focal plane if the intensity of the second elliptical feature is below the threshold intensity and below the focal plane if the intensity of the second elliptical feature is above the threshold intensity.

In accordance with a sixth aspect there is provided a method of automatically orienting an oocyte prior to intra-cytoplasmic sperm injection, the method comprising the steps of:
  i) detecting the orientation of the oocyte according to the method of the fifth aspect;
  ii) calculating rotations required to reposition the polar body of the oocyte in a predetermined orientation;
  iii) introducing a first suction holder along a first axis to hold the oocyte;
  iv) rotating the first suction holder to reorient the oocyte around the first axis;
  v) introducing a second suction holder along a second axis transverse to the first axis to hold the oocyte;
  vi) releasing the first suction holder from the oocyte; and
  vii) rotating the second suction holder to reorient the oocyte around the second axis.

In accordance with a seventh aspect there is provided a computer program comprising instructions for causing a computer to perform the method according to the fourth or sixth aspects. The computer program may be provided on a non-transitory medium such as a disc or read-only memory.

In accordance with an eighth aspect there is provided a method of intra-cytoplasmic sperm injection, comprising the steps of:
  holding an oocyte at a distal end of a suction holder, the suction holder comprising a lumen;
  passing an injection needle into the oocyte along the lumen of the suction holder;
  injecting a single sperm into the oocyte; and
  withdrawing the injection needle along the lumen of the suction holder.

The injection needle may be connected to a force sensor configured to measure force along an axis of the injection needle and a pressure differential between the oocyte and the lumen of the suction holder may be adjusted as a force detected by the force sensor rises upon contact between the injection needle and the oocyte.

The pressure differential may be automatically adjusted to counter the force detected by the force sensor.

The pressure differential may be automatically reduced upon detection of a reduction in force as the injection needle pierces the oocyte.

In accordance with a ninth aspect there is provided an intra-cytoplasmic sperm injection system, comprising:
  a suction holder for holding an oocyte, the suction holder having a lumen extending between a proximal and distal end, the distal end configured to hold an oocyte;
  a vacuum system connected to the lumen of the suction holder;
  an injection needle for introducing a single sperm, the injection needle having a central axis and proximal and distal ends, the distal end having an opening configured to inject a single sperm into an oocyte held by the suction holder; and
  an actuator connected to the proximal end of the injection needle and configured to actuate the injection needle in a direction along the central axis,
  wherein the suction holder is configured to allow a distal portion of the injection needle to be positioned within the lumen of the suction holder for injection of the single sperm into the oocyte.

The system may comprise a force sensor connected to the proximal end of the injection needle and configured to sense a force acting along the central axis of the injection needle.

The system may comprise a controller connected to the actuator, force sensor and vacuum system, the controller configured to adjust a pressure differential applied by the vacuum system between the lumen of the suction holder and an oocyte held by the distal end of the suction holder dependent upon a force acting on the injection needle sensed by the force sensor during injection of a sperm into the oocyte.

The controller may be configured to automatically adjust the pressure differential to counter the force detected by the force sensor.

The controller may be configured to automatically reduce the pressure differential upon detection of a reduction in force detected by the force sensor as the injection needle pierces the oocyte.

DETAILED DESCRIPTION

The invention is described in further detail below by way of example and with reference to the accompanying drawings, in which.

Figure 3A:
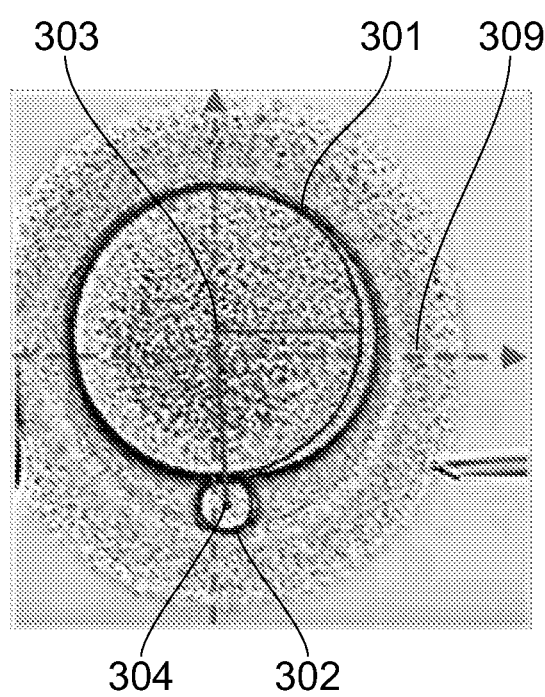
Figure 3B:
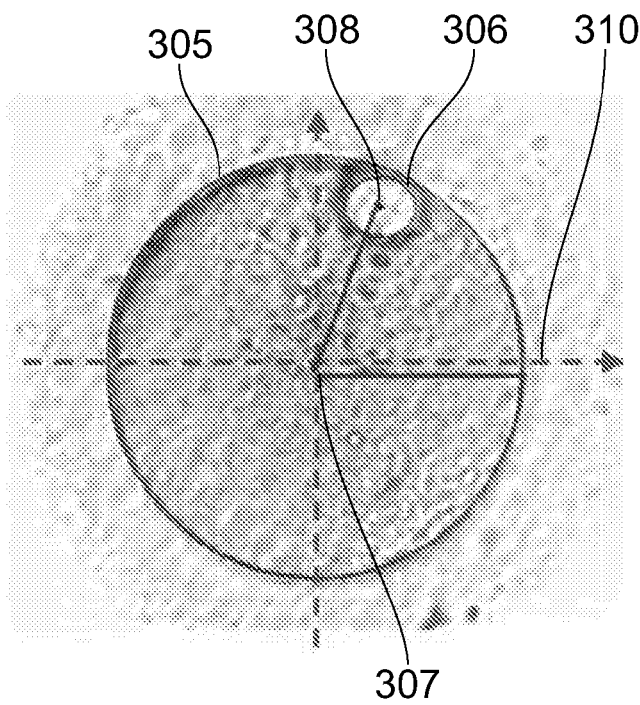
Figure 4:
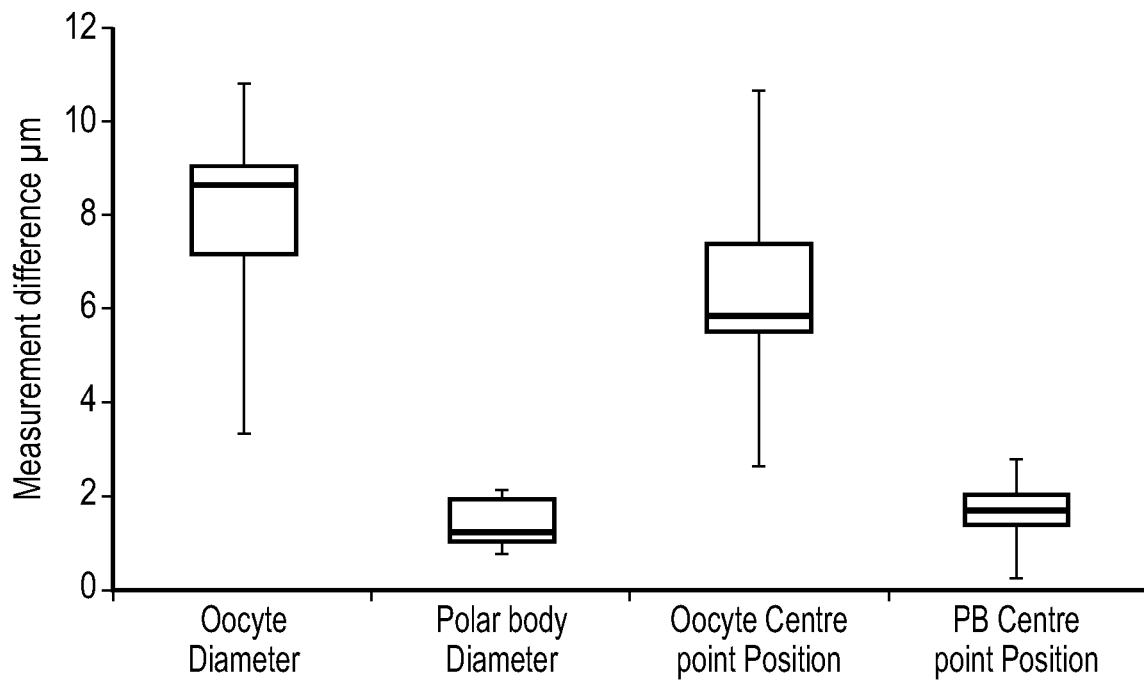
Figure 5:
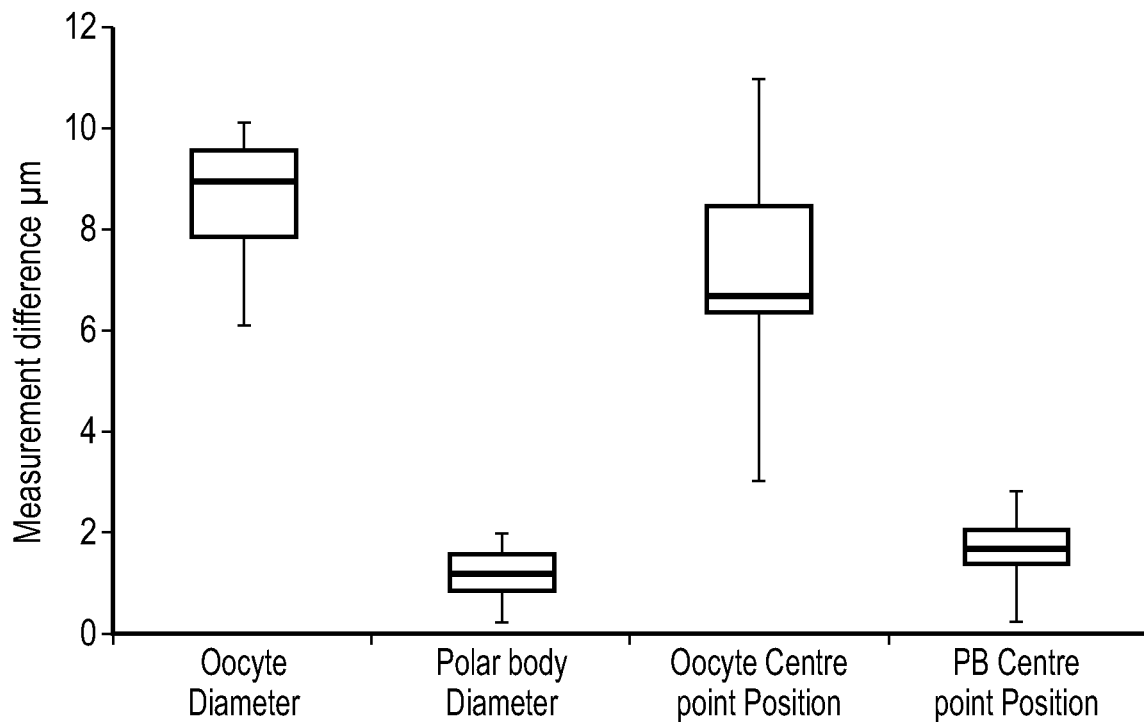
Figure 6:
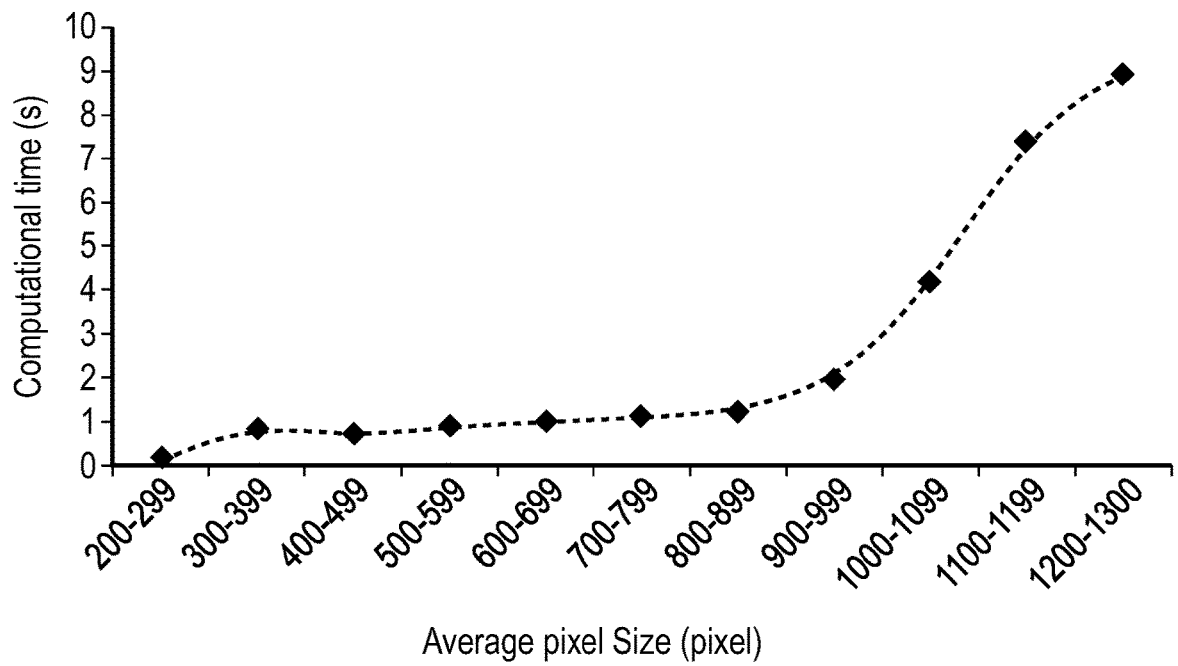
Figure 7A:
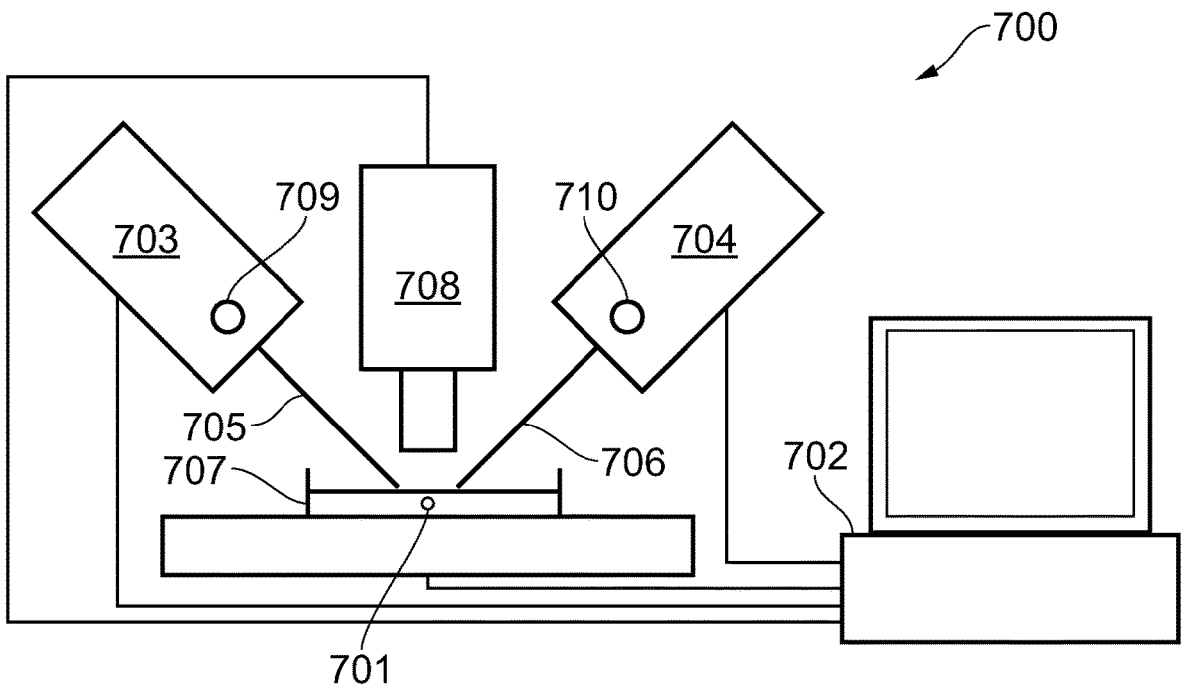
Figure 7B:
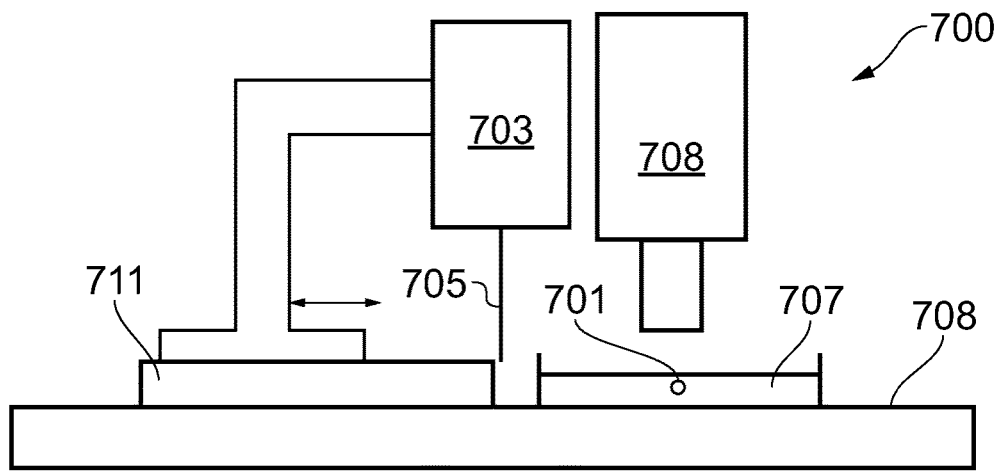
Figure 8:
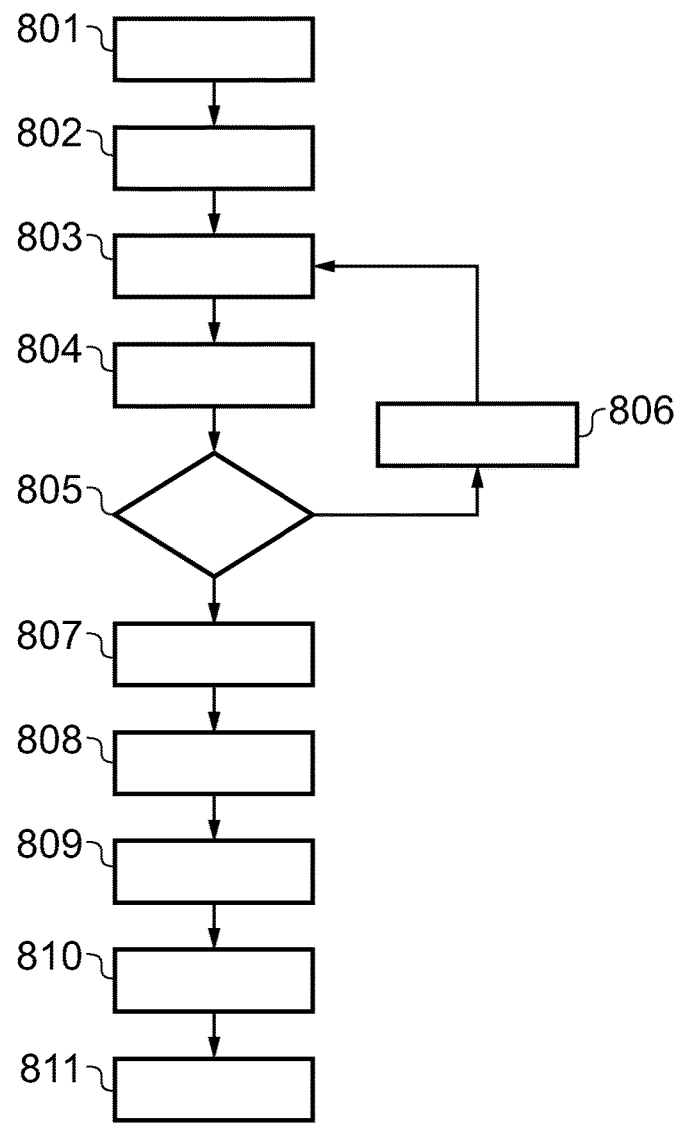
Figure 9A:
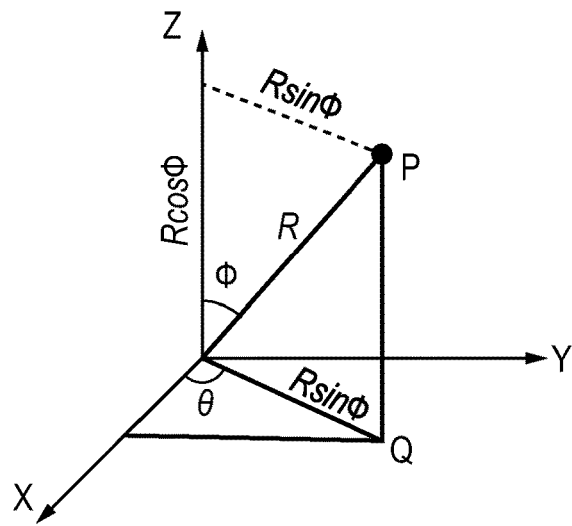
Figure 9B:
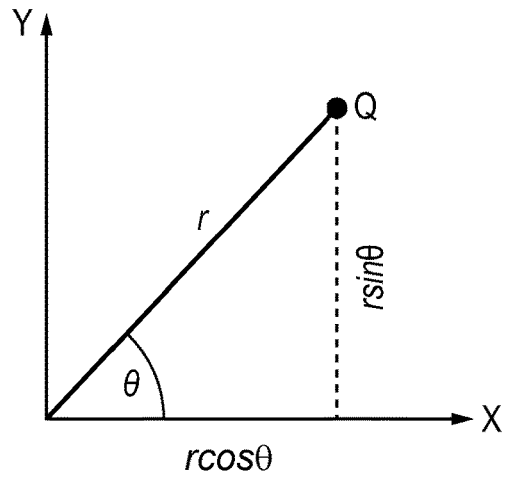
Figure 10:
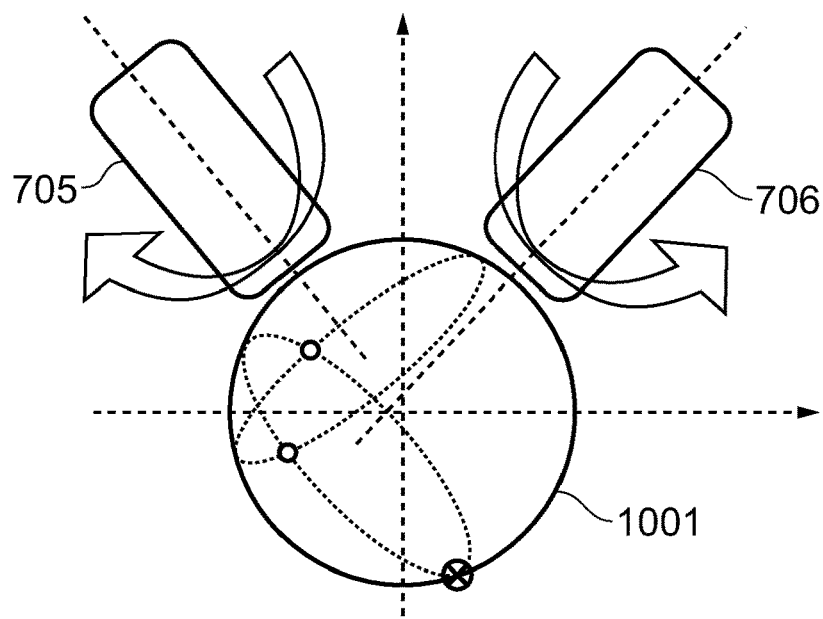
Figure 11:
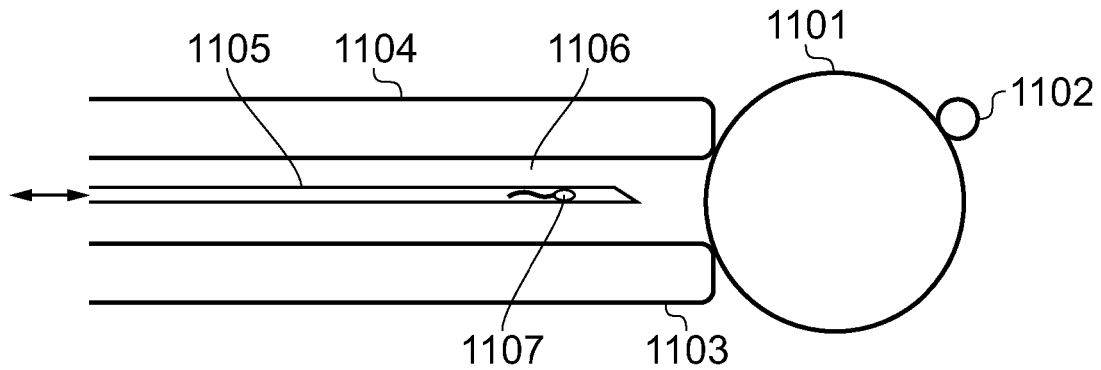
Figure 12A:
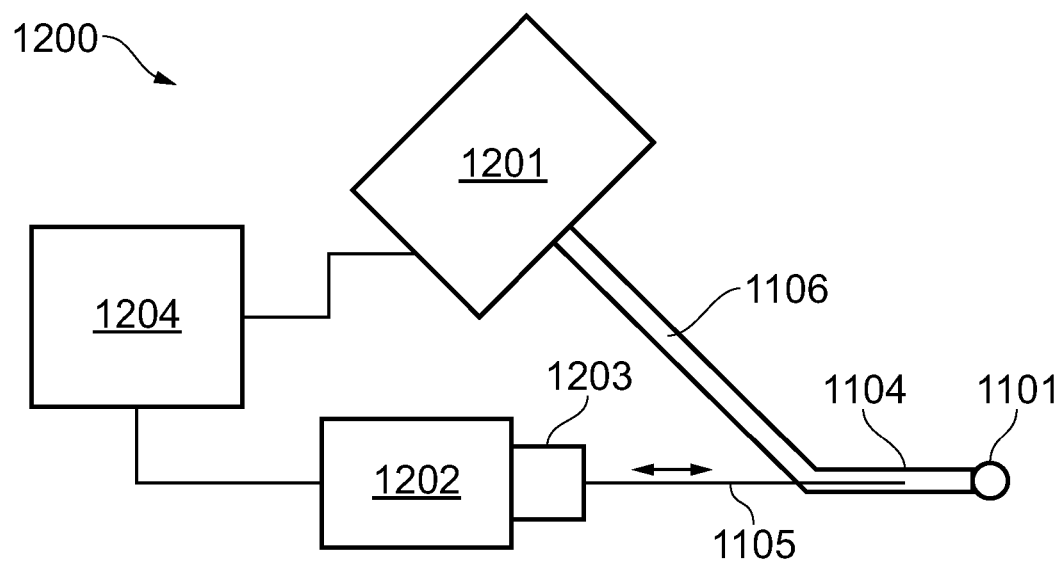
Figure 12B:
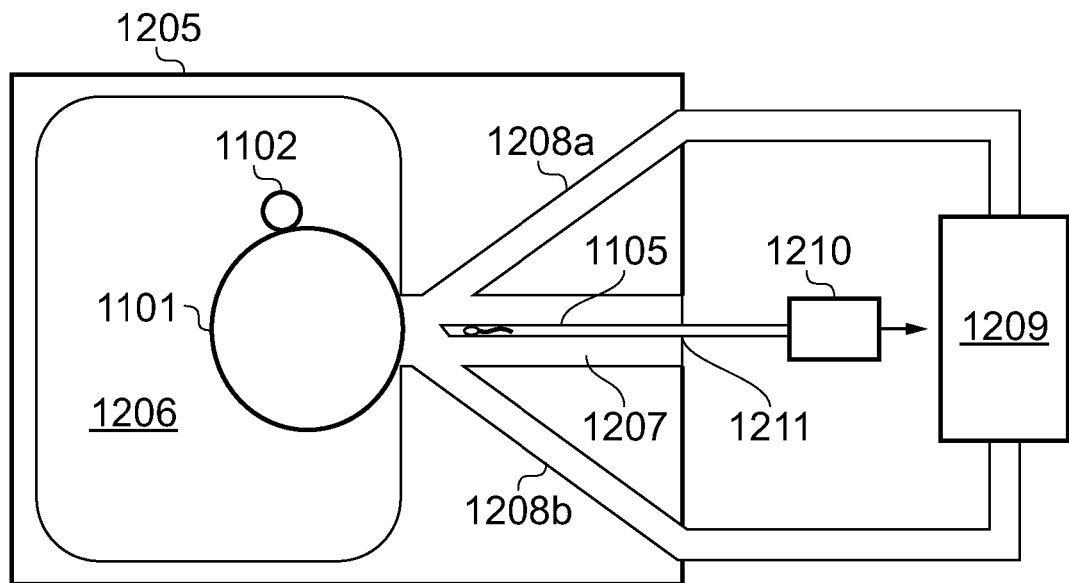
Figure 13:
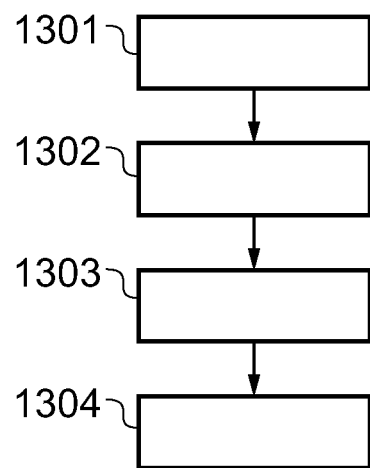
Figure 14:
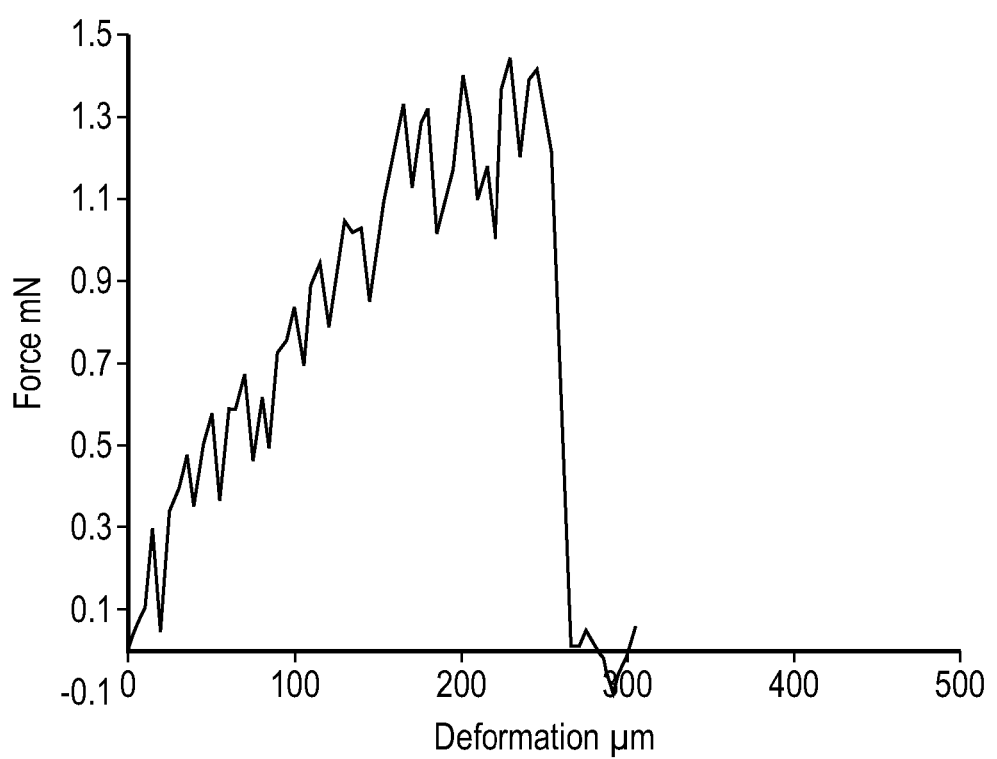
Figure 15:
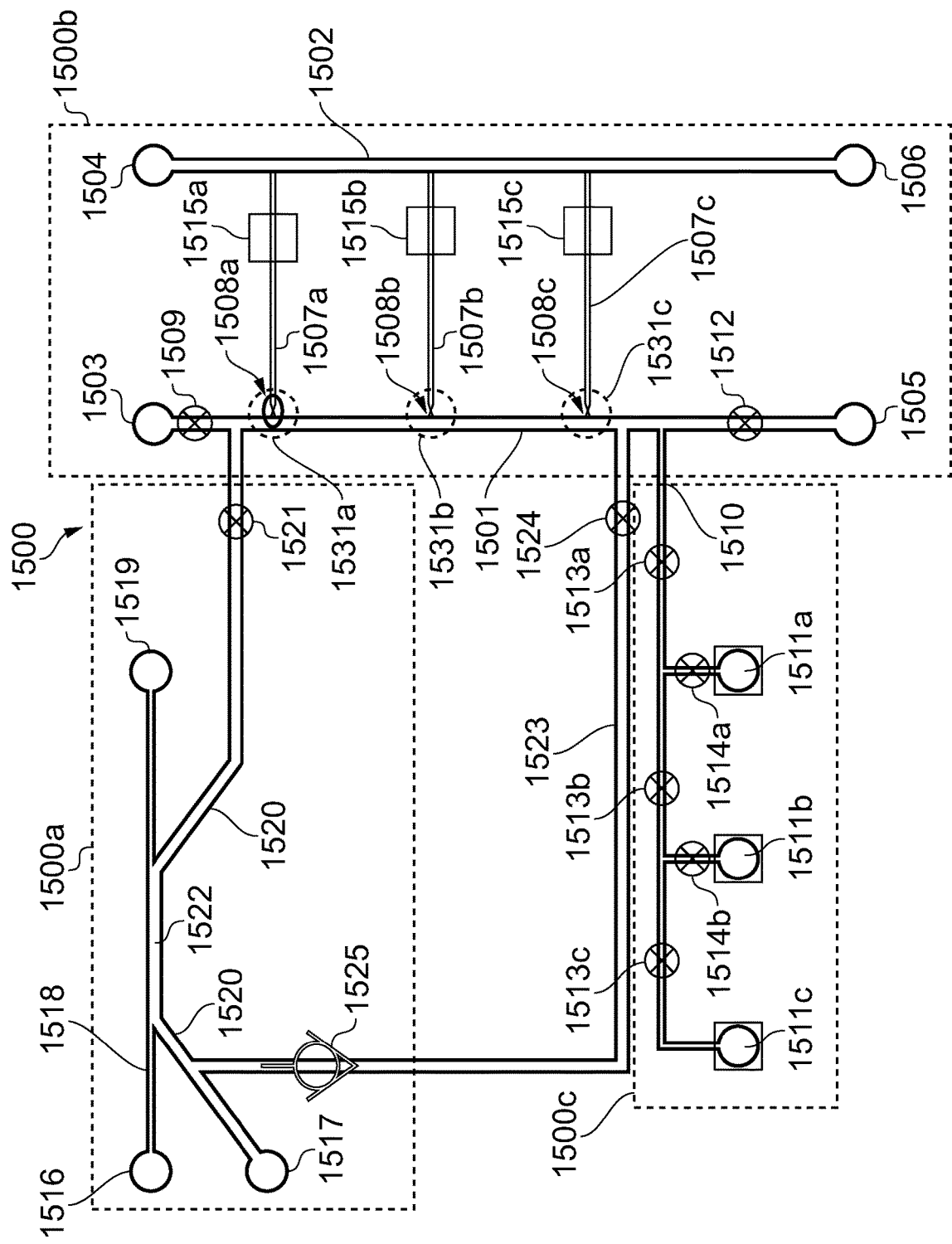
Figure 16:
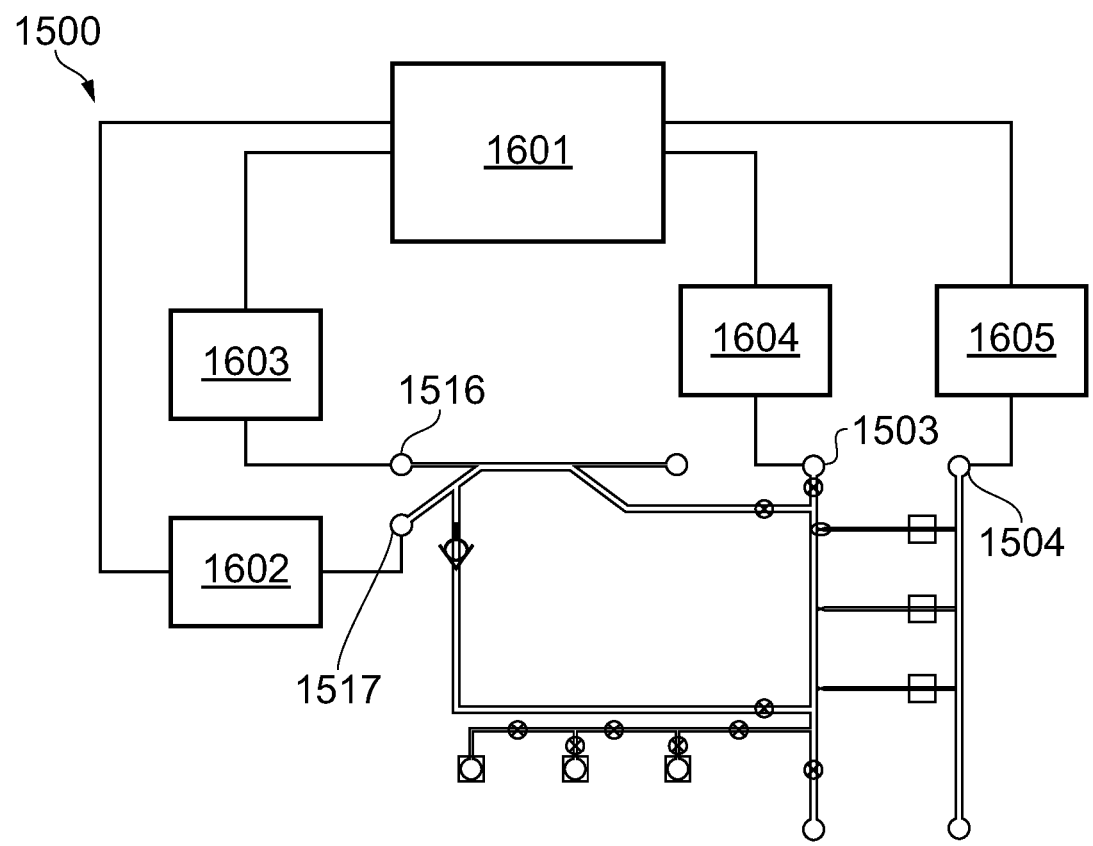
Figure 17:
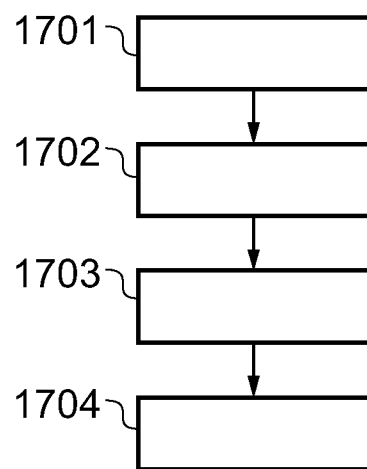

FIGS. 3*a* and 3*b* are example images of oocytes with overlaid markings indicating the position and orientation of the polar body relative to the oocyte;

FIGS. 4 and 5 are whisker plots of measurement differences between automatic and manual measurements of oocyte and polar body diameters and positions;

FIG. 6 is a plot of computational time as a function of image size;

FIGS. 7*a* and 7*b* are schematic diagrams of a system for image analysis and manipulation of an oocyte;

FIG. 8 is a schematic flow diagram of an example method of manipulating orientation of an oocyte;

FIGS. 9*a* and 9*b* are schematic diagrams showing a position of the centre of a polar body relative to the centre of an oocyte in three dimensions and in the focal plane of an image;

FIG. 10 is a schematic diagram illustrating a pair of suction holder manipulators relative to an oocyte;

FIG. 11 is a schematic diagram illustrating an example arrangement for injection of a single sperm into an oocyte;

FIG. 12*a* is a schematic diagram of an example system for injecting a single sperm into an oocyte;

FIG. 12*b* is a schematic diagram of an alternative example system for injecting a single sperm into an oocyte;

FIG. 13 is a schematic flow diagram of an example method of injecting a single sperm into an oocyte;

FIG. 14 is a plot of axial force on a microinjection needle as a function of time during injection into an oocyte;

FIG. 15 is a schematic diagram of a microfluidics system for isolation and capture of individual sperm from a semen sample;

FIG. 16 is a further schematic diagram of the microfluidics system of FIG. 15; and FIG. 17 is a schematic flow diagram of an example method of isolating and capturing an individual sperm from a semen sample.

OOCYTE ORIENTATION

Positioning and orienting the polar body in conventional ICSI is controlled by an embryologist. Currently, cell manipulation in conventional ICSI is manually operated by well-trained embryologists. The oocyte is manipulated by using a micropipette and inducing a negative pressure differential to hold and release the oocyte repeatedly until the polar body is positioned in the desired location. A single cell may be touched several times until it is in the desired place and prepared for injection. In cell manipulation, some researchers have tried to develop this into an automated process. Robotic cell manipulation with a good success rate and high degree of accuracy has been reported, but there are deficiencies in each method, such as not being able to correctly detect the oocyte. Other methods of manipulation may include microfluidic flow, optical tweezers and micromechanical grippers.

Cell detection is an essential method towards three-dimensional cell manipulation. In the proposed method described herein, image processing is focused on recognition of the oocyte and polar body. A first attempt at vision detection for cell manipulating purposes was designed to use morphological factors and Bayesian assessment as a classifier of texture and shape [92]. A major problem with this method is that it is computationally very expensive. Another method, the Hough cell detection algorithm (HCDA) utilises high pass filtering to detect the edges of the holding pipette and determine the oocyte size value [85]. In this method, however, polar body detection has not been developed. Again, the computational time for this method, of around 22 seconds, is high for a real-time application. Different algorithms have been proposed for detecting the polar body during the manipulation. However, the early stages of these detections recognized the polar body only when in plane [93]. This method involves the Otsu adaptive algorithm and morphological operator for fitting the circle to the cell. Otsu is a clustering-based image threshold technique which is employed to convert the greyscale image to a binary image. A linearization method was employed here for the polar body recognition [94]. The failure of this technique happens when the gray scale of the polar body and the oocyte are in the same level of surroundings in the image. Later, an algorithm was added to this method that estimated the polar body location out of plane using frame by frame motion analysis [93].

Image binarization is a method that may be used to detect the polar body. However, this method is highly dependent on the grey level of the neighbourhood pixels in the image. Inaccuracy occurs when the grey levels are similar in the surrounding pixels [85]. Another method of polar body detection was based on the polar body's texture data. Oocyte texture deficiencies and microscope light regulation limitation are two main disadvantages of this technique, which cause low accuracy [95]. Here the polar body and oocyte detections were proposed based on a machine learning method using image classification. In this method, the improved Histogram of Oriented Gradient (HOG) algorithm is used to extract features of polar body images for the prediction of the polar body position in the image, determination of this position, and finally detection [96, 97]. Recently, a method has been proposed for oocyte and polar body detection which employs template matching followed by morphological operations and thresholding [78]. The method is computationally expensive based on the sizes of the template and may need new templates.

Visual detection algorithms for the purpose of cell injection automation have involved the Hough transform to detect the polar body [98], roundness and elongation calculations following segmentation to detect the oocyte and injector respectively [99]; and a connected neighbourhood method for oocyte detection [100].

A new detecting technique for the oocyte and polar body has been developed using image detection rather than continuous frame tracking using video, employing a gradient-weighted Hough transform in the application of ICSI. In addition, a new method of gradient-based elliptical fitting has been developed [73], although this method has not resulted in a detection of orientation as well as positioning of the polar body.

Design of the software is based on combinations of the methods presented above. The images used for the software test were 8-bit JPEG compressed RGB images received from different types of inverted microscope cameras. All the images were converted to greyscale to save computational time for the subsequent steps. Linear contrast enhancement was employed to raise the dynamic range of the images to achieve better and easier edge detection [106].

A 5×5 weighted filter was applied to the images to minimize noise in the image and also restrain the granularity present in the polar body and oocyte. This filtering helps to reduce any possible false detection. The centre point position of the polar body and oocyte was detected by employing a weighted circular Hough transform method. The obtained gradient magnitudes were used as the weighting coefficient. To minimize calculation time, a limit was defined by the gradient magnitude threshold for the total of the edge points based on the centre point calculation.

As the software was designed to be compatible for different types of oocyte, the radius range for both the oocyte and polar body can be supplied by the user. This range was obtained from the literature for each iteration, or can be provided by the user. The centre point for both the oocyte and the polar body were extracted based on the developed algorithm. The microscope's lens' centre point was taken as the main reference point of the image. The circular Hough transform (CHT) was utilised for the oocyte and polar body detection in any position and for orientation in the image, which did not need to be in a close neighbourhood area in the centre of the image [107]. The elliptical Hough transform (EHT) was employed to detect an elliptical shape, in case the oocyte and/or polar body were this shape. It should be noted that the weighted Hough Transform was also sufficient for detecting the centre point, although the EHT tended to increase the accuracy of detection in possible elliptical shapes.

The sizes of the polar body and oocyte were detected after obtaining the location of the centre points. This was used as a combination with the elliptical fitting method. The radius for the elliptical fitting for the polar body and oocyte detection was determined by considering the specified radius ranges by the user. This method does not need the edge of the polar body and oocyte to be identified and has a better fitting in comparison to a circular fitting for the elliptical and ovoid shapes, and consequently provides more accurate sizing.

Figure 1:
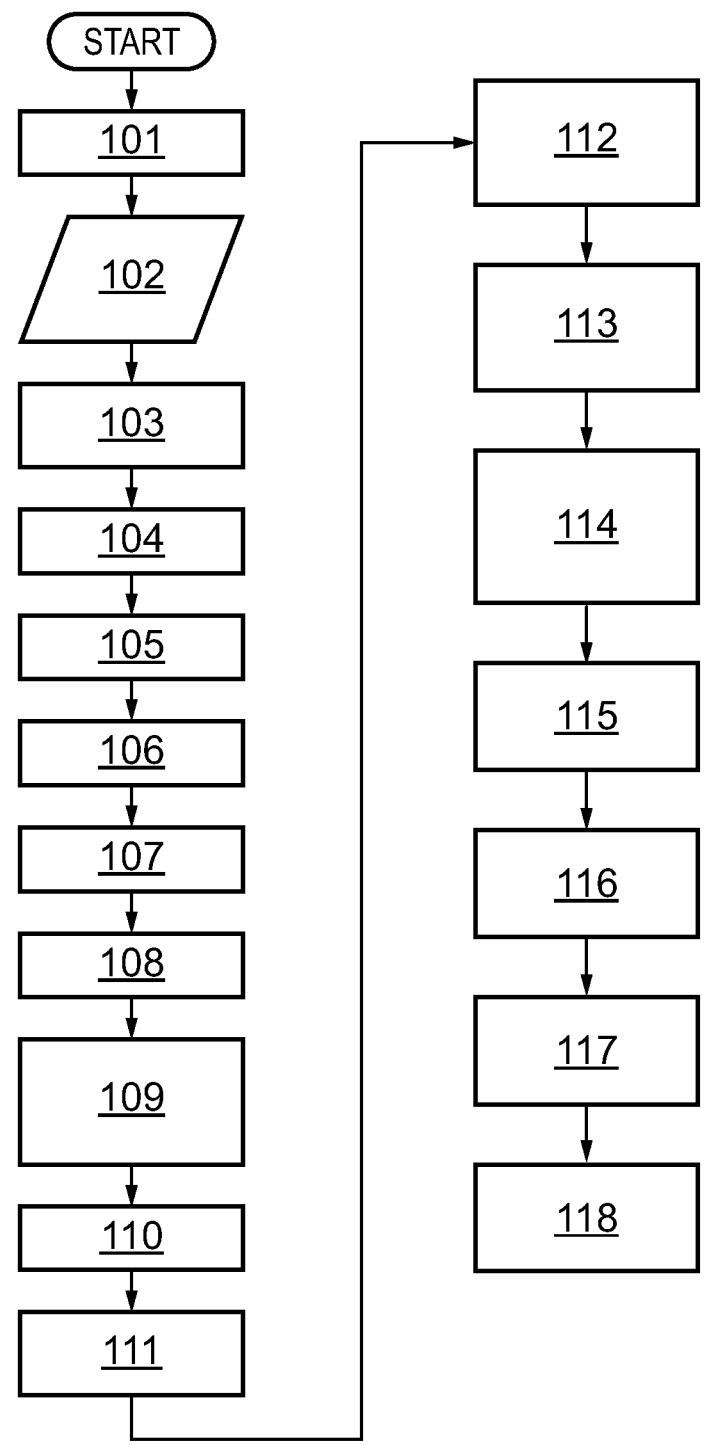
FIG. 1 is a schematic flow diagram illustrating an example method of analysing orientation of an oocyte from an image.

FIG. 1 illustrates a flow diagram illustrating a method of acquiring an image of an oocyte and determining its location and orientation. In a first step 101, the image detection program is run. The program then (step 102) requests a radius range of the oocyte and polar body radii for calibration. This step may be omitted if the program is used for only one type of oocyte, such as a human oocyte, where these dimensions and nominal ranges will be preset. An image of the oocyte is then taken (step 103) under the operator's supervision and control. Once the image is acquired, the image is converted from RGB to greyscale (step 104), linear contrast is enhanced (step 105) and a weighted average filter applied to the image (step 106). Image gradients Gx and Gy are then computed (step 107). The gradient magnitude is calculated (step 108) and pixel locations (edge points) are found where the gradient magnitude is above a threshold value (step 109). A weighted circular (or elliptical) Hough transform is then applied (step 110) and elliptical fitting used to detect the oocyte and polar body (step 111). Based on the known scale of the image, the size and centre point of the oocyte and polar body are converted into micron values (step 112), and the oocyte and polar body size (i.e. a diameter or radius) and centre points, together with a distance between the centre points, are output (step 113), which may be displayed on a graphical user interface along with the image. An angle of a connecting line between the polar body and oocyte centre points to a baseline is determined (step 114), which is used to calculate and output a two-dimensional orientation of the polar body (step 115). A further angle of a connecting line between the polar body and oocyte centre points relative to the focal plane of the image is then determined (step 116). If required, the obtained centre point coordinates and dimensions are rotated by 45 degrees (step 117), and the results are communicated on a graphical user interface (step 118). If further detection is required the process repeats, otherwise the process ends.

Figure 2:
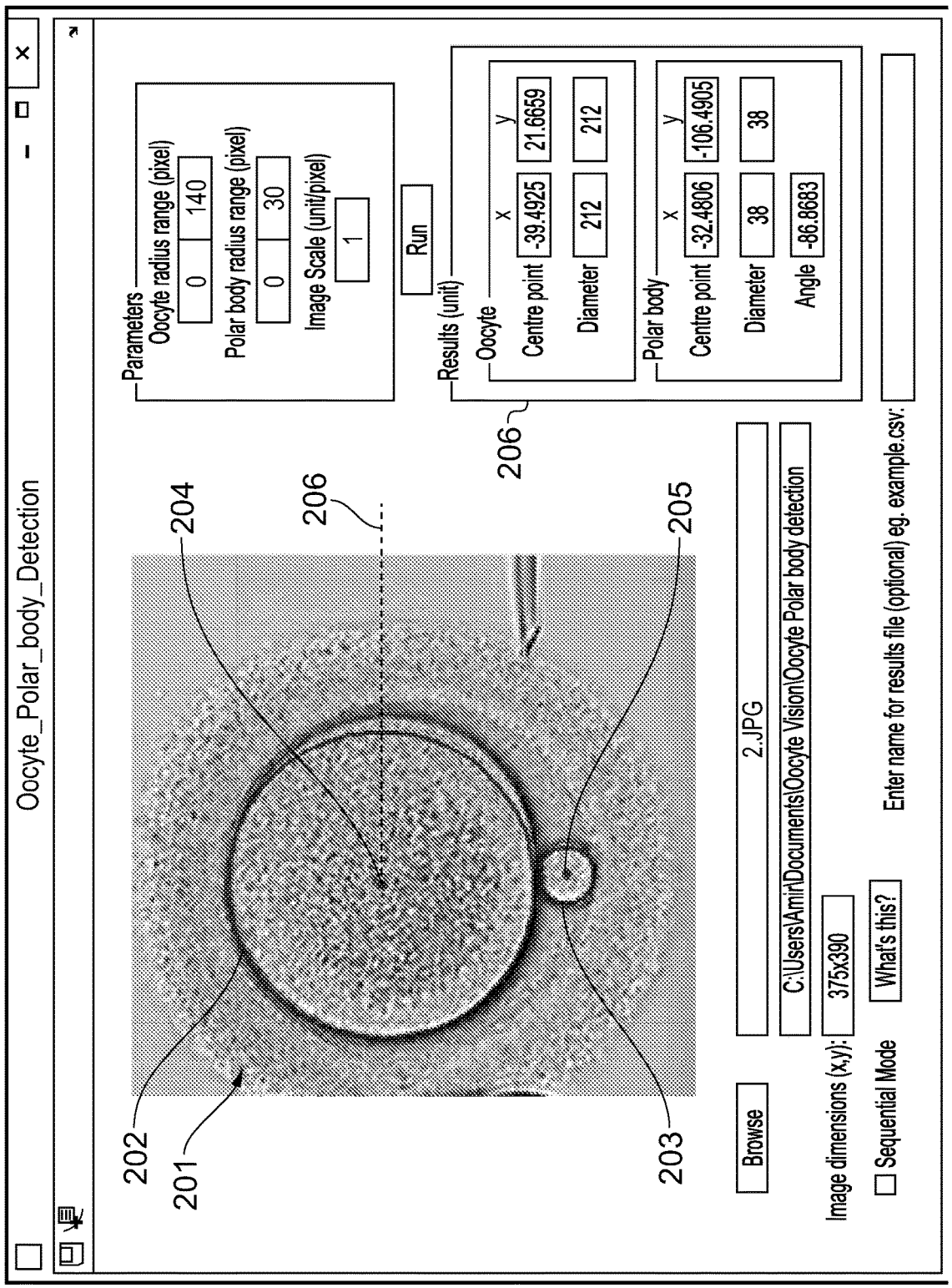
FIG. 2 is a screenshot of an example graphical user interface for image analysis of an oocyte.

A graphical user interface (GUI) may be used to enable initial information to be obtained from the operator and to show the results based on the calculation. The GUI asks about two parameter ranges, which enable the software to be compatible with different microscopes and different types of oocytes. Then, after pushing the 'RUN' button, the software follows the routing described above and outputs the specification of the oocyte and polar body, as indicated in FIG. 2. The oocyte 201 has been identified by first and second circles 202, 203, with corresponding centre points 204, 205, which are indicated in coordinates in a results box 206. The results box 206 also indicates the diameter of the oocyte 202, in this example 212 pixels, and the diameter of the polar body, in this case 38 pixels, together with an angular orientation in the focal plane of the image, which in this example is around −87 degrees. The angular orientation is calculated relative to a baseline, which may for example be a horizontal line 206 extending from the calculated centre point 204 of the oocyte 202. In the illustrated example, a positive angle indicates anticlockwise orientation of the polar body relative to the baseline 206, and a negative angle indicates a clockwise orientation of the polar body relative to the baseline 206.

Information output from the algorithm described above is then fed into a further routine to determine the location and orientation of the polar body and oocyte in global coordinates. This information indicates the position and the diameter of the oocyte and polar body centres as well as the angle where the polar body's centre 205 is positioned with respect to positive direction of X-Axis, or baseline 206.

FIGS. 3a and 3b illustrate two examples of images of an oocyte with overlaid fitted circles where the oocyte and polar body have been detected. In FIG. 3a, the position of the polar body 302 relative to the oocyte 301 is such that the centre points 303, 304 are approximately in the focal plane of the image, since the fitted circle 302 of the polar body is coincident with the fitted circle 301 of the oocyte. In FIG. 3b, however, the position of the centre point 308 of the polar body 306 as being within the fitted circle 305 of the oocyte indicates that the polar body is out of the focal plane. In each case an angular orientation of the polar body relative to a horizontal baseline 309, 310 extending from the centre points 303, 307 of the oocyte are indicated. This angular orientation, however, only indicates the orientation in the focal plane. Orientation out of the focal plane also needs to be determined to determine the three dimensional orientation of the polar body relative to the oocyte.

Experiments were conducted for various images sourced from numerous microscopes. These images were considered as input to the software and the software first detected the polar body and oocyte. If the polar body was not in the focal zone of the microscope, then the software gave a message about not locating a polar body. After confirmation of the correct recognition of the polar body and oocyte, the sizes of the oocyte and polar body were computed. The sizes of both the polar body and oocyte were then measured manually using ImageJ software (a public domain image processing programme developed for image analysis in biomedical applications) to validate the software functionality.

The algorithm has been tested with different factors that may have an impact on the results. Eighty images have been tested for each major factor set. Table 1 below summarises results comparing 240 different images taken from different resources. The first row indicates the images taken from different microscopes with a different background colour. It shows 100% correct detection on these types of sampling test. The second row images of different orientations of a polar body which were taken from the same microscope. The polar bodies are located in random locations in the perivitelline space. This test indicates the ability of the software to detect orientation and position of the polar body in a space. A 100% successful detection has been reported for this set as well. The third row shows different microscope zooms. This test has been done to check the ability of the software to detect the polar body and oocyte under different magnifications. This test also had a 100% success rate. The last row points out the failure of the software in this type of image; this is because the images were blurred and clarity of the image was poor. Also there were some disturbances in the image which were considered as noise and these were the cause the failures. Despite these disturbances, the oocyte was detected successfully in each case and the failures happened only for detection of the polar body.

In summary, the oocyte and polar body detection algorithm is capable of being adopted generally by different types of inverted microscopes. Existing extra cumulus cells are known to disturb the outcome of the algorithm and may cause some errors in the detection of the polar body due to its smaller size. However, the existence of these cells have been shown not to have any effect on oocyte detection. To reduce the possibility of not correctly detecting the polar body by image analysis, the oocyte should be denudated prior to image analysis.

TABLE 1

Comparison table for all tested images

| Description | Total tested images | Correct Oocyte detection | Correct polar body detection | Correct Oocyte location detection | Correct polar body location detection |
| --- | --- | --- | --- | --- | --- |
| Different background colour | 80 | 80 100% | 80 100% | 80 100% | 80 100% |

TABLE 1-continued

Comparison table for all tested images

| Description | Total tested images | Correct Oocyte detection | Correct polar body detection | Correct Oocyte location detection | Correct polar body location detection |
|---|---|---|---|---|---|
| Different position and orientation | 80 | 80 100% | 80 100% | 80 100% | 80 100% |
| Different magnification of the images | 80 | 80 100% | 80 100% | 80 100% | 80 100% |
| With disturbances | 20 | 20 100% | 12 60% | 20 100% | 12 60% |

Different microscopes operate with different vision background colours based on the type and purpose of the operation. FIG. 4 is a whisker chart illustrating the differences in measurements using different background colours. The highest differences between manual and software measurement was for oocyte diameter measurements. The average oocyte diameter and polar body are 140 μm and 20 μm respectively, and the corresponding maximum error for oocyte diameter measurements are approximately 5% and 10% respectively.

The oocyte is positioned on the petri dish at random, which results in random positioning of its polar body. The algorithm was nonetheless capable of detecting the centre point of the oocyte and that of its polar body, and calculating a line that connects these two points. Successful detection was achieved for all of the 240 test images used, excluding those where image disturbances were detected, and for 252 out of a total of 260 including images with disturbances. Validation with ImageJ software also confirmed accuracy of the oocyte and polar body diameter and centre point measurements, as shown in FIGS. 4 and 5. This illustrates that the majority of the differences for the oocyte diameter and positioning are less than 10 μm, and for polar body are approximately 2 μm.

Computational time for detecting the oocyte and polar body was found to be highly dependent on the quality and size of the image based on the pixels. After 240 experiments, the relationship shown in FIG. 6 was obtained showing the computational time. This shows computational time with respect to the average size of the images. The computational time for images with the average amount of 900 pixels was 1±0.2 seconds. For the majority of the acceptable quality images, the computational time was 0.8 seconds, although if the number of pixels increased to more than 1000, the computational time suddenly significantly increased. The overall size of the image in pixels is therefore preferably fewer then around 1200 in either dimension, or fewer than around 1.44 million pixels in total (i.e. 1200×1200) for an acceptable computational time of a few seconds or less. For a computational time of 2 seconds or less, a maximum image dimension of 1000 pixels (i.e. 1 million pixels in total) is preferable.

Oocyte Manipulation

Interaction between a manipulator and a cell may lead to mechanical stress on the cell membrane. Due to sensitive interaction between a manipulator and a cell, cell micromanipulation systems have been developed to prevent or minimise potential damage [108-112]. Micromanipulation may be defined as a combination of tools and techniques for the purpose of cell rotating and positioning. Micromanipulation techniques play an important role in the development of devices in assisted reproductive technology [13]. There are different applications for three-dimensional rotation and manipulation of biomaterials in biomedical applications such as ICSI, polar body biopsy and cloning [82-84, and 86].

Currently, cell manipulation in conventional ICSI has been manually operated by well-trained embryologists. The oocyte is manipulated by using a micropipette and applying negative pressure [114] to hold and release the oocyte frequently until the polar body is positioned in the desired location. This type of manipulation is known as a trial-and-error course of action [74]. The method of sucking the cell with negative pressure can be utilized to model the cell with an aspiration technique. There are various research projects focusing on automating 3D manipulations of biological cells [125-128]. Robotic cell manipulation has been reported in a few publications with a considerable success rate and high accuracy [79, 117]. However, there are some deficiencies introduced in each method, such as lack of correct detection.

Automating the manipulation of an oocyte in collaboration with injection and integrating a vision detection system have been focused on during the last decade [134-137]. Although there have been many researchers working in this area, still there are some difficulties in the manipulation methods, as well as in the integration of the vision software and manipulation in addition to the injection process.

The system described herein is capable of cell manipulation, following which injection takes place after oocyte delivery to a stationary holder. The system comprises a two-armed robotic manipulator on a three-dimensional micro controlled stage (8MT167 motorised stages, Standa Ltd.), arranged to manipulate a single oocyte and deliver it to re-position the cell in a stationary holder in the correct orientation using a minimum number of oocyte interactions. The system further comprises an integrated automated injector which conducts the injection. The system enables manipulation and injection in one unit, which makes the system compact. The manipulator is attached to a controller which integrated with a vision recognition algorithm for detecting the polar body and oocyte position and orientation and providing the initial coordinates for controlling the manipulator. The manipulator delivers the oocyte after manipulation to a stationary holder, after which injection takes place. The system is also capable of being incorporated into existing ICSI lab equipment without needing to change any essential features of the microscope.

FIGS. 7a and 7b illustrate a schematic diagram of an example system 700 for automatically orienting an oocyte 701 prior to intra-cytoplasmic sperm injection, with FIG. 7a a view from the front of the system 700 and FIG. 7b a partial side view. The system 700 comprises a controller 702 (typically a general purpose computer) connected for control of first and second micromanipulators 703, 704 having respective first and second suction holders, or pipettes, 705, 706 directed towards a container 707 containing the oocyte 701. A microscope 708 is positioned over the container (petri dish) 707 for viewing the oocyte 701 during manipulation and subsequent injection. A light source (not shown) is provided below the container so that the oocyte 701 can be viewed by the microscope 708 in transmitted light. Each manipulator 703, 704 is configured to move the respective pipette 705, 706 along its axis and rotate about its axis. The manipulators 703, 704 are mounted to a common two or three axis stage 711 (FIG. 7b), which allows for fine scale movement of the manipulators 703, 704 relative to the oocyte 701. Each manipulator 703, 704 comprises a respective vacuum connection 709, 710 to provide a pressure differential between the pipette 705, 706 and the oocyte 701 to allow the oocyte 701 to be held at a distal end of the pipette 705, 706. As shown in FIG. 7b, the manipulators 703, 704 (one of which is shown in this side view) are mounted on a common three axis stage 711 to allow for fine scale movement of the manipulators. The stage 711 also allows the manipulators to be moved towards and away from the microscope 708, which allows the manipulators to be incorporated into current ICSI microscope systems. In alternative arrangements, the microscope 708 and container 707 may be mounted on a stage to move relative to the manipulators 703, 704 for fine scale movement of the oocyte.

Each manipulator 703, 704 operates on two modes of coarse and fine movement. In an example embodiment, to provide linear movement in coarse motion, a hybrid stepper motor (RVFM MY5602 Mini Hybrid Stepper Motor Size 14) was connected to a lead screw with a 1 mm pitch. The main advantage of using a stepper motor is to eliminate the necessity of having an encoder, as it can be controlled in an open-loop manner by controlling the steps, as there is otherwise a chance of missing a step. The step angle of the chosen stepper motor was 1.8 degree/step with a holding torque of 8 Ncm. As each step of the stepper motor is rotating 1.8 degrees of a circle, a whole rotation takes 200 steps. A micro-stepping driver can be employed in conjunction with the stepper controller in case a smaller angle is required. However, there is no need for micro stepping as that may add errors such as vibration to the system. As the pitch for the lead-screw is 1 mm, then each step will operate with a movement of 5 μm. Fine motions are enabled by the motorised stage 711, which may have a finer degree of accuracy, for example around 1 μm.

Rotational movement is provided by a servo motor (Dynamixel MX-28R Robot Actuator) on each manipulator 703, 704. The oocyte 701 is held by a negative pressure using a commercial micro-holder, which is connected to the servo motor through a suction chamber for the purpose of rotational manipulation. For operation, the micro-holder 705, 706 is inserted into a hollow shaft through an adaptor made of rubber where the shaft is placed in a vacuum chamber to prevent any leakage of air. This is significant as any air loss will cause a reduction in the negative pressure and end with the loss of the cell. Thus, the vacuum area is absolutely sealed to waive this problem. The vacuum is created in the chamber by using a suction pipe attached to the manipulator 703, 704, which is connected to a controllable dynamic suction pump (not shown). The shaft of the micro-holder is then connected to the servo motor on the other end. The servomotor is able to provide rotational movement of the micro-holder ±180 degrees.

Operation of the manipulator system 700 may be fully automated after receiving a start order from an operator. The system functionality is divided into four main steps: i) oocyte positioning; ii) oocyte recognition; iii) oocyte manipulation and delivery to a stationary holder; and iv) oocyte injection. An example series of method steps is illustrated in FIG. 8.

The process starts (step 801) when an oocyte is deposited somewhere in the focal zone of microscope, after being denudated. Once the oocyte is positioned in the view of the microscope 708, (step 802), automated cell recognition then begins. Polar body position and orientation are recognised (step 803) and the locational information of the polar body and oocyte is provided to the controller of the manipulator, as described in further detail above in relation to FIG. 1. The system may then request the final orientation information from the user, or may alternatively use preset orientation information (step 804). The process of determining the position and orientation of the oocyte and polar body may take up to 2 seconds, depending on the size of the image used. One of the manipulators 703, 704 is then operated to bring a respective sample holder 705, 706 into contact with the oocyte 701 (step 805).

The two manipulators 703, 704 are arranged to be transverse to one another, and preferably aligned to be orthogonal to one another. Consequently, the system 700 allows for two rotational degrees of freedom, which allows the oocyte to be oriented in any position. The system 700 is designed to manipulate using a minimum of two operations if the polar body is detected correctly, and with a maximum of four operations if not. Incorrect polar body detection may be caused by confusion in the polar body orientation which may be on either the top or bottom of the oocyte, as viewed under the microscope. This is because of transparency of the cell and using an inverted vision system. The correct position of the polar body may be checked after the oocyte has been reoriented using the manipulators to ensure that the correct initial position of the polar body was detected. The initial position of the polar body may be determined by the intensity of the detected shape of the polar body in a greyscale image, given that the intensity will tend to be lower (i.e. darker) if the polar body is on top, and higher (i.e. lighter) is the polar body is underneath. An intensity threshold may therefore be used to determine whether the polar body is above or below the focal plane of the image, with the polar body being determined to be above if the intensity of the polar body is below the threshold and below the focal plane if the intensity of the polar body is above the threshold. Where the intensity of the polar body is close to or at the threshold, the polar body is likely to be at or near the focal plane, and a miscalculation is less likely to have a significant effect on subsequent reorientations to place the polar body in a desired position.

After rotational manipulation by the first manipulator 703, the oocyte 701 is delivered to the second manipulator 704 for a further rotational manipulation orthogonal to the first. Before manipulation there are three possibilities for the position of the polar body in the focal zone of the microscope 708:

1. Polar body is visible and detected correctly by the software;
2. Polar body is not visible;
3. Polar body is detected wrongly.

In each of the above conditions, a specific operation may be defined for the system 700. If the polar body is visible and detected correctly (step 805), then the standard procedure takes place and the main operation starts (step 807 in FIG. 8). If the polar body is not visible, then one of the manipulators contacts the oocyte and rotates it by 90 degrees. The process of detecting and determining orientation then repeats (step 803). This procedure repeats until the polar body is brought into the vision field of the microscope. Once the polar body is detected, the main operation starts (step 807). For the last stage of polar body detection, the user may need to confirm if the system has detected the polar body correctly. If the polar body is detected incorrectly and the user does not verify the detection, the software may repeat the examinations and select an alternative potential feature considered if the polar body does not exist in the image.

Each oocyte usually has a circular shape when viewed under the microscope. In some exceptional circumstances, the oocyte can be slightly deformed and have an elliptical shape. For the purpose of this description it is assumed that the oocyte is perfectly spherical and a perfect circle in the images (although the vision system will be capable of detecting an elliptical oocyte). In the case of an exceptional condition, then the mean of the diameters of the elliptical shape may be considered as the diameter of the circle.

The manipulation calculation is carried out (step 807 in FIG. 8) with reference to the centre point of the oocyte with respect to global coordinates and the polar body with respect to local coordinates of the oocyte. The polar body centre is located on the perimeter of an imaginary sphere 1001 having a radius which is the sum of the calculated radii of the oocyte and its polar body, as shown in FIG. 10. Consequently, the polar body centre point coordinate needs to be calculated in volumetric dimensions from the information received from the image analysis software. FIG. 9a illustrates a three axis representation of the centre point P of the polar body at a radius R from the centre point of the oocyte. A line connecting the centre points subtends an angle φ to the z axis, while a line projected on to the x-y axis plane (i.e. the focal plane of the image) subtends an angle θ to the x axis, which is also shown in FIG. 9b, where point P is projected on to point Q. The information shown in FIG. 9b is received from the image analysis software. The radius R can be calculated from a sum of the calculated radii of the oocyte and the polar body, while the projected radius r is the distance in the focal plane between the calculated centre of the oocyte and the calculated centre of the polar body. The angle φ to the z axis can then be readily calculated using the following relationship:

$$\phi = \text{Arcsin}\left(\frac{r}{R}\right)$$

This defines the centre position of the polar body in polar coordinates, which can be used to calculate rotations required to reposition the polar body in any desired orientation. As illustrated in FIG. 10, the sample holders 705, 706 are able to rotate the oocyte 1001 about two orthogonal axes. After calculating the rotations required to reorient the polar body to the required position, the sample holders 705, 706 are brought sequentially into contact with the oocyte and rotated through the required angles (steps 808, 809). The polar body should then be in the required position. A further check may then be carried out to ensure that the polar body is in the desired location. If the polar body is not in the correct location, an error may have occurred, which can be reported to the user and the procedure halted. If the polar body is in the correct location, once manipulation has concluded the oocyte is then delivered to a stationary holder to initiate the injection procedure (step 810), and the manipulators return back to their home position (step 811).

Injection Procedure

After finalising the manipulation steps of the oocyte, the oocyte is delivered to a stationary holder, which is defined for the system as the final point, and the injection procedure starts. The final location of the sperm delivery may then be selected by the user, or alternatively be predefined.

Sperm deposition plays an important role in the success rate of the ICSI. Once this is defined, the system delivers to the aimed location with minimum damage to the oocyte using optimum factors. The oocyte can then be released to be moved to an incubator after conducting the injection.

FIGS. 11 and 12a illustrate schematically an example system for injecting a single sperm into an oocyte. FIG. 11 shows a detailed view of the oocyte 1101, with polar body 1102, held to a distal end 1103 of a vacuum sample holder 1104. An internal lumen 1106 of the holder 1104 is sized to allow for passage of a microinjector needle 1105, through which a single sperm 1107 may be injected into the oocyte 1101.

As shown in FIG. 12a, the sample holder 1104 is attached to a vacuum system 1201 for creating a pressure differential between the internal lumen 1106 and the oocyte 1101 to keep the oocyte 1101 in position at the distal end 1103 of the sample holder 1104. The vacuum system 1201 is operated under control of a controller 1204, which may be the same as the controller 702 for the manipulators, microscope and stage 708 on which the oocyte 1101 is positioned. The controller 1204 also controls operation of an actuator 1202, which operates to actuate the needle 1105 along its longitudinal axis. A force sensor 1203 is provided to measure force along the axis of the needle 1105. The needle enters into the internal lumen 1106 of the sample holder 1104 via an airtight seal.

FIG. 12b shows a schematic detailed view of an example chamber 1205 for holding an oocyte 1101 with its polar body 1102 in a desired position ready for injection by a microneedle 1105. The chamber 1205 comprises a petri dish 1206 for containing the oocyte 1101 and a lumen 1207 for applying a suction to the oocyte 1101 to hold it in position. A vacuum is applied to the lumen 1207 by a vacuum pump 1209 via one or more channels 1208a, 1208b extending transversely from the lumen 1207. A force sensor 1210 is connected to the microneedle 1105 for sensing axial force as the microneedle is actuated axially to penetrate the oocyte 1101 membrane. A vacuum seal 1211 is provided across the lumen 1207 to form a seal between the microneedle 1105 and the lumen 1207.

Operation of the ICSI system 1200 may proceed according to the flow diagram in FIG. 13. To start the operation (step 1301), the oocyte 1101 is held at the distal end 1103 of the suction holder 1104. The injection needle 1105 is then passed along the lumen 1106 of the suction holder 1104 into the oocyte 1101 (step 1302). The single sperm 1107 within the needle 1105 is then injected into the oocyte 1101 (step 1303), and the needle 1105 is withdrawn along the lumen 1106 of the suction holder 1104. The oocyte may then be transferred to an incubation chamber (step 1304).

The force sensor 1203 enables a force along an axis of the injection needle 1105 to be measured, and thereby enables a pressure differential applied by the vacuum system 1201 to be adjusted as a force detected by the force sensor 1203 rises upon contact between the injection needle 1105 and the oocyte 1101. FIG. 1400 shows an example plot of force measured along the axis of an injection needle during penetration into a zebrafish oocyte, with a penetration speed of 1 micron per second. The force rises from initial contact with the oocyte as the oocyte is deformed by up to around 250 microns, at which point the force rapidly falls to around zero as the needle penetrates the oocyte. The combination of a force sensor 1203 with an adjustable vacuum system 1201 therefore enables the force being applied by the needle to be automatically balanced by increasing the pressure as the measured force rises. The pressure differential rise required, Δp, over the pressure required to hold the oocyte in place, can be readily calculated from the diameter, d, of the internal lumen and the force, F, measured on the needle, such that Δp=Fd. Deformation of the oocyte membrane can thereby be reduced or minimised, potentially reducing damage to the oocyte. As an example, a suction pressure of around 2.5 kPa may be used to initially hold the oocyte in place. Once the microneedle has been detected as touching the oocyte membrane, the suction pressure is increased as the microneedle is moved forward into the oocyte. As soon as the microneedle has been detected as having pierced the oocyte membrane, which is detectable by a sudden drop off in force, the suction pressure is reduced. Once the microneedle is in place, the sperm is injected into the oocyte. The microneedle is then withdrawn while the oocyte is held in place with a minimum suction pressure.

Sperm Isolation and Delivery

To perform ICSI, a single sperm needs to be selected, isolated and drawn into an injection needle for delivery to an oocyte. Current methods for ICSI typically involve an embryologist manually selecting a sperm, which can result in significant difference in success rates depending on operator skill and judgement. The system and method described herein is intended to remove operator dependency, and instead relies on an automated microfluidics system to isolate a single motile sperm from a sample of semen.

FIG. 15 is a schematic diagram of a microfluidics system 1500 for isolating individual sperm from a semen sample. The system 1500 has a sperm separation section 1500a, a sperm isolation section 1500b and a sperm capture section 1500c. The operation of each section is described below.

The isolation section 1500b of the system 1500 comprises first and second laminar flow channels 1501, 1502 extending between respective first and second inlets 1503, 1506 and first and second outlets 1505, 1504. In the arrangement shown, the flow direction in the first laminar flow channel 1501 is opposite to the flow direction in the second laminar flow channel 1502. This allows for successive release of sperm trapped in restrictions 1508a-c from respective 1507a-c, as described in further below. For trapping and releasing of a single sperm, however, the direction of flow in laminar flow channels 1501, 1502 may be the same or opposite. A third laminar flow channel 1507a extends between the first and second laminar flow channels 1501, 1502, the third laminar flow channel 1507a having a restriction 1508a configured to prevent passage of a single sperm. Further laminar flow channels 1507b, 1507c may be provided, also extending between the first and second laminar flow channels 1501, 1502 and each having a restriction 1508b, 1508c configured to prevent passage of a single sperm. Each of the laminar flow channels 1507a-c can thereby isolate a single sperm. The number of channels is a matter of design choice depending on how many individual sperm are required to be isolated. The restriction 1508a-c in each case is preferably located proximate the first laminar flow channel 1501 so that it is only possible for a single sperm to enter each channel before it becomes trapped.

During operation of the system 1500, fluid containing sperm flow along the first laminar flow channel 1501 towards the first outlet 1505, while a further fluid flow is present between the second inlet 1504 and second outlet 1506. A pressure differential between the fluids flowing in the first and second laminar flow channels 1501, 1502 is maintained such that the pressure in the second laminar flow channel 1502 is lower than the pressure in the first laminar flow channel 1501. This results in a proportion of fluid flowing within the first laminar flow channel 1501 being drawn into the third fluid flow channel 1507a. Once a sperm enters the third fluid flow channel 1507a, it becomes trapped within the restriction 1508a and fluid flow through the third fluid flow channel 1507a stops, or at least significantly reduces, as a result. Fluid flow continues through the first fluid flow channel 1501 until all sperm have passed through the channel 1501 to the first outlet 1505. Any further fluid flow channels 1508b, 1508c may also capture a single sperm, reducing the flow through each channel 1508b, 1508c.

Valves 1509 and 1512 are initially closed. This allows all sperm to be circulated via the first laminar flow channel 1501 until each of the restrictions 1508a-c has trapped a single sperm. Once a flow rate reduction is detected in each of the flow channels 1507a-c, valves 1521 and 1524 both close while valves 1509 and 1512 are opened, allowing fluid to flow into the first flow channel 1501 through the first inlet 1503. This maintains a pressure difference between the first and second laminar flow channels 1501, 1502, holding the sperms in place in the restrictions 1508a-c while the first laminar flow channel 1501 is flushed with fluid. Simulation measurements indicate that the time taken to flush the first laminar flow channel 1501 completely is around 40 seconds. Once the first laminar flow channel 1501 is flushed, valve 1512 closes and valves 1513a, 1514a open. The pressure is then increased from the inlet 1506.

Once capture of a single sperm has been confirmed in each of the flow channels 1507a-c, valves 1521, 1524 are closed and valves 1509, 1512 opened in order to flush out excess cells. Simultaneous to this, additional valves 1531a-c located over each of the restrictions 1508a-c may be provided in the system 1500, the additional valves 1531a-c being closed in order to immobilise the sperm in each restriction 1508a-c and break their membrane. Once flushing has been complete the additional valves 1531a-c may be opened to allow successive release of the entrapped sperms to begin.

In the sperm capture section 1500c, a fourth laminar flow channel 1510 is connected between the first laminar flow channel 1501 and a third outlet 1511a, the third outlet 1511a serving to capture a sperm trapped in one of the restrictions 1508a-c. Further outlets 1511b, 1511c may be provided, each connected to the fourth laminar flow channel 1510, for capturing further individual sperm. Once sperm have been trapped in each of the restrictions 1508a-c and the remaining sperm flowing through the first laminar flow channel 1501 have exited through the first outlet 1505, a second valve 1512 in the first laminar flow channel 1501 between the fourth laminar flow channel 1510 and the first outlet 1505 is closed. A third valve 1513a in the fourth laminar flow channel 1510 between the first laminar flow channel 1501 and the third outlet 1511a is then opened. Pressure in the second laminar flow channel 1502 then causes flow through the third laminar flow channel 1507a to reverse, and the sperm trapped in the restriction 1508a is released to flow along the first laminar flow channel 1501 towards the third outlet 1511a. Any sperm trapped in other restrictions 1508b, 1508c that may be present are also released and flow along the first fluid flow channel 1501.

In the illustrated example, three restrictions 1508a-c are present, situated at different points along the first fluid flow channel 1501. Once the fluid flow in each of the respective channels 1507a-c reverses, and the additional valves 1531a-c opened (if present), the sperm trapped in each restriction 1508a-c will travel in series along the first fluid flow channel. A sperm trapped in restriction 1508c will therefore be the first to reach the third outlet 1511a. Once this sperm has reached the third outlet 1511a, a fourth valve 1514a in the fourth laminar flow channel 1510 between the third outlet 1511a and the first flow channel 1501 is closed.

The sperm is then trapped within the third outlet 1511a. A fifth valve 1513b may then be opened to allow fluid in the fourth laminar flow channel 1510 to travel towards a fourth outlet 1511b until a further sperm is trapped in the fourth outlet 1511b, at which point a sixth valve 1514b is closed to trap the sperm in the fourth outlet 1511b. A seventh valve 1513c may then be opened to allow fluid in the fourth laminar flow channel 1510 to travel towards a fifth outlet 1511c until a further sperm is trapped in the fifth outlet 1511c, at which point the seventh valve 1513c may be closed, trapping the sperm in the fifth outlet 1511c.

Each of the third, fourth and fifth outlets 1511a-c may be coated with a sperm-immobilising protein to cause a sperm trapped in the outlet to slow down or stop moving. An antisperm antibody such as the protein Immunoglobulin G isotype may be used, which has been found to lead to up to a 90% reduction in motility when this antibody is present in the cervix, as for example reported by Chiu et al, in Fertility and Sterility September 2004, Volume 82, Issue 3, Pages 529-35. Each of the outlets 1511a-c may be in the form of a chamber that is coated according to a process described by Sin et al (Biotechnology and Bioengineering, Volume 91, Issue 7, 30 Sep. 2005, pages 816-826). According to this process, the chamber is flushed using a silane solution in ethanol. Unreacted silane is then removed by washing again in ethanol. The chambers is then flushed again with GMBS solution and allowed to react. Then after flushing with ethanol again the chambers are finally flushed with Neutravidin solution and stored. After being in a fridge overnight the antibodies are allowed to flow through the chamber and then washed finally.

In a general aspect therefore, a microfluidics system for containing and immobilising an individual sperm may comprise a chamber connected to a laminar flow channel for introduction of the individual sperm in a carrier fluid, wherein an internal surface of the chamber is coated with an antisperm antibody. The antisperm antibody may for example be an Immunoglobulin G isotype.

A flow sensor 1515a-c may be provided in each fluid flow channel 1507a-c connecting the first and second fluid flow channels 1501, 1502. The flow sensors 1515a-c may be thermal mass flow meters, which measure a mass flow rate based on a measurement of temperature change of fluid passing through the meter as it is heated. The flow sensor 1515a-c is configured to sense when fluid flow stops, which indicates that a sperm has been trapped in a respective restriction 1508a-c. Once fluid flow has stopped in each channel 1507a-c, it is known that each of the restrictions contains a trapped sperm.

A movement sensor 1516a-c may be provided at each of the third, fourth and fifth outlets 1511a-c to sense when a sperm is introduced into each outlet, enabling a signal to be generated to determine when to open and close valves 1514a, 1514b, 1513b. 1513c.

The sperm separation section 1500a of the system 1500 is configured to separate motile from non-motile sperm. A third inlet 1516 is provided for the introduction of a semen sample into the system 1500, and a fourth inlet 1517 is provided for introduction of a fluid transport medium. A fifth laminar flow channel 1518 extends between the fourth inlet 1516 and a sixth outlet 1519. A sixth laminar flow channel 1520 extends between the fourth inlet 1517 and the first laminar flow channel 1501. An eighth valve 1521 is provided in the sixth laminar flow channel to enable flow from the sixth laminar flow channel 1520 into the first laminar flow channel 1501 to be controlled.

A mixing chamber 1522 is provided that joins the fifth and sixth laminar flow channels 1518, 1520 between the third inlet 1516 and sixth outlet of the fifth laminar flow channel and between the fourth inlet 1517 and first laminar flow channel 1501 of the sixth laminar flow channel 1520. The width of the mixing chamber 1522 is equal to the sum of the widths of the fifth and sixth laminar flow channels 1518, 1520, so no fluid mixing occurs between the channels 1518, 1520. The mixing chamber does, however, allow motile sperm carried in the fifth channel 1518 to transfer from the laminar flow in the fifth channel 1518 to laminar flow in the sixth channel 1520. Any non-motile sperm, or sperm with a sufficiently low motility, will not transfer from the fifth to sixth channel, and will therefore continue in the fifth channel 1518 towards the outlet 1519. As a result, only sperm of sufficient motility that, by random movement, transfer from the fifth to sixth laminar flow channel will continue in the sixth channel 1520 towards the first laminar flow channel 1501. All other sperm will be separated and removed from the system 1500 via the sixth outlet 1519.

A seventh laminar flow channel 1523 may be provided between the first laminar flow channel 1501 and the fourth inlet 1517, the return path comprising a ninth valve 1524 and a check valve 1525. The seventh laminar flow channel 1523 allows for sperm to recirculate through the first laminar flow channel 1501 until sperm are trapped in each of the restrictions 1508a-c, which might not be achieved in a single pass.

A further schematic diagram of the microfluidics system 1500 is shown in FIG. 16, in which additional control and pumping components are illustrated. A controller 1601 is connected for control of pumps 1602-1605 and operation of each of the valves in the system 1500. The controller 1601 also receives input signals from each of the flow sensors 1515a-c and movement sensors 1511a-c. A first pump 1602 is connected to the fourth inlet 1517 for introduction of a fluid transport medium into the system 1500. A second pump is connected to the third inlet 1516 for introduction of a semen sample into the system 1500. A third pump 1604 is connected to the first inlet 1503 for introduction of a fluid transport medium into the first laminar flow channel 1501. A fourth pump 1605 is connected to the second inlet 1504 for introduction of a fluid transport medium into the second laminar flow channel 1502.

The microfluidics system 1500 may be incorporated, optionally with or without the controller 1601, on to a single microfluidics device, or microfluidic chip (also known as a "lab-on-a-chip"). The system 1500 may also be incorporated together with an oocyte handling chamber, such as a chamber 1205 of the type described above and illustrated in FIG. 12b, to enable a complete ICSI operation to be performed using an integrated system. Human intervention may then be required only for introduction of an oocyte and introduction of a semen sample. Operation of the system may then be partially or entirely automated.

Flow of fluids through the various laminar flow channels of the system 1500 may be controlled using controllable microfluidics valves and electromechanical pumps that may be integrated with the system. Examples of such integration are disclosed by Blanco-Gomez et al in Analytical Chemistry, 2009, 81(4), pp 1365-1370, Suzuki & Yoneyama in *Sensors and Actuators B: Chemical,* Volume 95, Issues 1-2, 15 Nov. 2003, pages 38-45, and by Zhao et al in *Scientific Reports* 7, Article number 11319 (2017), among others. An example of a complete microfluidics lab-on-a-chip is disclosed in *Lab Chip,* 2014, 14, 2168, in which a chip is mounted on top of a silicon chip, which can interrogate data measured from sensors in the microfluidics device. A further example of a lab-on-a-chip is disclosed by Xie et al in 56th Electronic Components and Technology Conference 2006, San Diego, CA, 2006, doi: 10.1109/ECTC.2006.1645732.

Example operation of the sperm isolation section 1500b of the system 1500 is illustrated in the flow diagram of FIG. 17. In a first step 1701, a semen sample is introduced into the first laminar flow channel 1501 at a first pressure, optionally after separation from an initial sample into a motile and non-motile portion. In a second step 1702 (which may be performed simultaneously to the first step 1701), a fluid transport medium is introduced into the second laminar flow channel at a second pressure lower than the first pressure. In a third step 1703, following the first and second steps 1701, 1702, a single sperm is trapped in the restriction in the third laminar flow channel. This causes a reduction in flow through the third laminar flow channel. The first and second valves are then closed (step 1704), and the third valve is opened, causing the trapped sperm to travel to the third outlet for collection.

Other embodiments are intentionally within the scope of the invention as defined by the appended claims.

The invention claimed is:

1. A microfluidics system for isolating individual sperm from a semen sample, the system comprising:
a first laminar flow channel extending between a first inlet and a first outlet;
a second laminar flow channel extending between a second inlet and a second outlet;
a third laminar flow channel extending between the first and second laminar flow channels and having a restriction configured to prevent passage of a single sperm through the third laminar flow channel, wherein flow of a semen sample through the first laminar flow channel at a pressure higher than flow of a liquid medium through the second laminar flow channel results in a single sperm being trapped by the restriction in the third laminar flow channel;
a fourth laminar flow channel connected between the first laminar flow channel and a third outlet;
a first valve in the first laminar flow channel between the first inlet and the third laminar flow channel;
a second valve in the first laminar flow channel between the fourth laminar flow channel and the first outlet;
a third valve in the fourth laminar flow channel between the first laminar flow channel and the third outlet,
wherein, upon closing the first and second valves and opening the third valve, a sperm trapped by the restriction in the third laminar flow channel travels to the third outlet for collection;
a flow sensor configured to sense fluid flow in the third laminar flow channel;
a first pump arranged to pump fluid into the first inlet at a first pressure;
a second pump arranged to pump fluid into the second inlet at a second pressure lower than the first pressure; and
a controller configured to control the first and second pumps, operate the first, second and third valves and receive a flow signal from the flow sensor,
wherein the controller is configured to close the first and second valves upon detecting a reduction in flow through the third laminar flow channel from the flow sensor and to open the third valve to cause fluid from the second laminar flow channel to flow through the third laminar flow channel, the first laminar flow channel and towards the third outlet.

2. The system of claim 1 wherein the third outlet comprises a chamber with an internal surface coated with an antisperm antibody.

3. The system of claim 2 wherein the antisperm antibody is an Immunoglobulin G isotype.

4. A method of operating a microfluidics system, the system comprising:
system comprising:
a first laminar flow channel extending between a first inlet and a first outlet;
a second laminar flow channel extending between a second inlet and a second outlet;
a third laminar flow channel extending between the first and second laminar flow channels and having a restriction configured to prevent passage of a single sperm through the third laminar flow channel, wherein flow of a semen sample through the first laminar flow channel at a pressure higher than flow of a liquid medium through the second laminar flow channel results in a single sperm being trapped by the restriction in the third laminar flow channel;
a fourth laminar flow channel connected between the first laminar flow channel and a third outlet;
a first valve in the first laminar flow channel between the first inlet and the third laminar flow channel;
a second valve in the first laminar flow channel between the fourth laminar flow channel and the first outlet;
a third valve in the fourth laminar flow channel between the first laminar flow channel and the third outlet,
wherein, upon closing the first and second valves and opening the third valve, a sperm trapped by the restriction in the third laminar flow channel travels to the third outlet for collection;
a flow sensor configured to sense fluid flow in the third laminar flow channel;
a first pump arranged to pump fluid into the first inlet at a first pressure;
a second pump arranged to pump fluid into the second inlet at a second pressure lower than the first pressure; and
a controller configured to control the first and second pumps, operate the first, second and third valves and receive a flow signal from the flow sensor,
wherein the method comprises:
introducing a semen sample into the first laminar flow channel at a first pressure;
introducing a fluid transport medium into the second laminar flow channel at a second pressure lower than the first pressure;
trapping a single sperm in the restriction in the third laminar flow channel; and
controlling the controller to close the first and second valves upon detecting a reduction in flow through the third laminar flow channel from the flow sensor and to open the third valve to cause fluid from the second laminar flow channel to flow through the third laminar flow channel, the first laminar flow channel and towards the third outlet.

5. The method of claim 4 wherein the system comprises a flow sensor configured to sense fluid flow in the third laminar flow channel, wherein detecting a reduction in flow through the third laminar flow channel comprises receiving a signal from the flow sensor.

6. The method of claim 4 wherein the system comprises a fifth valve over the restriction, the method comprising closing the fifth valve following trapping the single sperm in the restriction.

7. The method of claim 4 wherein the system comprises a fifth valve over the restriction, the method comprising closing the fifth valve following trapping the single sperm in the restriction and opening the fifth valve prior to opening the third valve to cause the sperm trapped by the restriction in the third laminar flow channel to travel to the third outlet for collection.

\* \* \* \* \*